(12) United States Patent  (10) Patent No.: US 6,620,170 B1
Ahern  (45) Date of Patent: Sep. 16, 2003

(54) DEVICES AND METHODS FOR TREATING ISCHEMIA BY CREATING A FIBRIN PLUG

(75) Inventor: John E. Ahern, Melrose, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/299,795

(22) Filed: Apr. 26, 1999

(51) Int. Cl.$^7$ ................................................ A61F 2/06
(52) U.S. Cl. ...................................... 606/108; 128/898
(58) Field of Search ................... 623/1, 1.42; 128/898; 264/485, 279, 279.1; 606/108

(56) References Cited

U.S. PATENT DOCUMENTS

| | | |
|---|---|---|
| 3,680,544 A | 8/1972 | Shinnick et al. |
| 4,326,522 A | 4/1982 | Guerrero et al. |
| 4,894,057 A | 1/1990 | Howes ........................ 604/280 |

(List continued on next page.)

FOREIGN PATENT DOCUMENTS

| | | | |
|---|---|---|---|
| DE | 19703482 | | 8/1998 |
| EP | 207438 | * | 1/1987 |
| EP | 0 490 459 A1 | | 6/1992 |
| EP | 0 717 969 A2 | | 6/1996 |
| EP | 0 876 803 A2 | | 11/1996 |
| EP | 0 830 873 A2 | | 3/1998 |
| EP | 0 853 921 A2 | | 7/1998 |
| EP | 0 953 320 A2 | | 11/1999 |
| FR | 1278965 | * | 1/1961 |
| FR | 1514319 | | 5/1968 |
| FR | 2725615 | * | 10/1994 |
| WO | WO 90/06723 | | 6/1990 |
| WO | WO 94/27612 | | 12/1994 |
| WO | WO 95/33511 | | 12/1995 |
| WO | WO 96/20698 | | 7/1996 |
| WO | WO 97/38730 | | 10/1997 |
| WO | WO 97/42910 | | 11/1997 |
| WO | WO 97/45105 | | 12/1997 |
| WO | WO 98/23228 | | 6/1998 |
| WO | WO 98/29148 | | 7/1998 |
| WO | WO 99/21510 | | 5/1999 |
| WO | WO 99/38459 | | 8/1999 |
| WO | WO 99/53863 | | 10/1999 |
| WO | WO 99/55252 | | 11/1999 |
| WO | WO 00/18325 | | 4/2000 |
| WO | WO 00/18326 | | 4/2000 |

OTHER PUBLICATIONS

Sporn et al., "Cell Proliferation on Fibrin: Modulation by Fibrinopeptide Cleavage", Blood, vol. 86, No. 5, pp. 1802–1810, Sep. 1995.*

(List continued on next page.)

*Primary Examiner*—Cary E. O'Connor
(74) *Attorney, Agent, or Firm*—Kirkpatrick & Lockhart LLP

(57) ABSTRACT

The present invention provides devices and methods for inducing fibrin growth in tissue to promote revascularization of that tissue. The devices and methods are useful in ischemic tissue occurring anywhere in the body, and are particularly useful in treating ischemic myocardial tissue of the heart. The device may comprise a frame configured to foster a fibrin growth and configured to permit communication between the fibrin and the tissue into which the frame is implanted. The fibrin may be positioned internally or externally on the frame. The implant should be capable of becoming anchored in the tissue to prevent the formed fibrin from dislodging from the tissue. A fibrin producing substance may be associated with the implant device to help promote and sustain the fibrin growth. Alternatively, a thrombophilic or fibrin producing substance may be introduced into ischemic tissue alone, without an associated device, to induce fibrin growth in vivo. In another aspect of the invention, a thrombus formed ex vivo may be associated with the device prior to implantation to aid in revascularization by initiating angiogenesis and vessel recruitment. A thrombus formed ex vivo also may be introduced into the subject tissue without an associated implant device.

29 Claims, 14 Drawing Sheets

U.S. PATENT DOCUMENTS

| | | | |
|---|---|---|---|
| 4,904,264 A | 2/1990 | Scheunemann | 623/18 |
| 5,180,366 A | 1/1993 | Woods | 604/96 |
| 5,366,493 A | 11/1994 | Scheiner et al. | 607/116 |
| 5,429,144 A | 7/1995 | Wilk | 128/898 |
| 5,510,077 A * | 4/1996 | Dinh et al. | 623/1 |
| 5,562,922 A | 10/1996 | Lambert | 424/486 |
| 5,609,629 A * | 3/1997 | Fearnot et al. | 623/1 |
| 5,653,756 A | 8/1997 | Clarke et al. | 623/11 |
| 5,810,836 A | 9/1998 | Hussein et al. | 606/108 |
| 5,824,049 A | 10/1998 | Ragheb et al. | 623/11 |
| 5,851,217 A | 12/1998 | Wolff et al. | 606/191 |
| 5,861,032 A | 1/1999 | Subramaniam | 623/11 |
| 5,879,383 A | 3/1999 | Bruchman et al. | 623/11 |
| 5,957,971 A * | 9/1999 | Schwartz | 606/200 |
| 5,971,993 A | 10/1999 | Hussein et al. | 606/108 |
| 5,980,514 A | 11/1999 | Kupiecki et al. | 606/32 |
| 5,980,548 A | 11/1999 | Evans et al. | 606/185 |
| 6,045,565 A | 4/2000 | Ellis et al. | 606/167 |
| 6,053,924 A | 4/2000 | Hussein | 606/108 |
| 6,197,324 B1 | 3/2001 | Crittenden | 424/423 |
| 6,248,112 B1 | 6/2001 | Gambale et al. | 606/108 |
| 6,251,418 B1 | 6/2001 | Ahern et al. | 424/423 |
| 6,263,880 B1 | 7/2001 | Parker et al. | 128/898 |
| 6,277,082 B1 | 8/2001 | Gambale | 600/549 |
| 6,432,126 B1 | 8/2002 | Gambale et al. | 623/1.1 |
| 6,447,522 B2 | 9/2002 | Gambale et al. | 606/108 |
| 6,458,092 B1 | 10/2002 | Gambale et al. | 604/22 |

OTHER PUBLICATIONS

Neil B. Ingels, et al., Measurement of Midwall Myocardial Dynamics in Intact Man by Radiography of Surgically Implanted Markers, Circulation, vol. 52, pp. 859–867 (Nov. 1975).

U.S. patent application Ser. No. 09/073,118, Gambale, filed May 5, 1998.

U.S. patent application Ser. No. 09/159,834, Cafferata, filed Sep. 24, 1998.

U.S. patent application Ser. No. 09/162,547, Gambale, filed Sep. 29, 1998.

U.S. patent application Ser. No. 09/211,332, Gambale et al., filed Dec. 15, 1998.

U.S. patent application Ser. No. 09/328,808, Ahern, filed Jun. 9, 1999.

U.S. patent application Ser. No. 09/743,695, Weiser et al., filed Apr. 12, 2001.

U.S. patent application Ser. No. 09/743,726, Gambale et al., filed Apr. 12, 2001.

U.S. patent application Ser. No. 09/744,319, Gambale et al., filed Jan. 31, 2001.

U.S. patent application Ser. No. 09/744,320, Gambale et al., filed Jan. 31, 2001.

U.S. patent application Ser. No. 09/888,757, Ahern et al., filed Jun. 25, 2001.

U.S. patent application Ser. No. 09/990,644, Gambale et al., filed Nov. 21, 2001.

U.S. patent application Ser. No. 10/048,205, Gambale, filed May 2, 2002.

U.S. patent application Ser. No. 10/048,694, Gambale et al., filed Jun. 10, 2002.

* cited by examiner

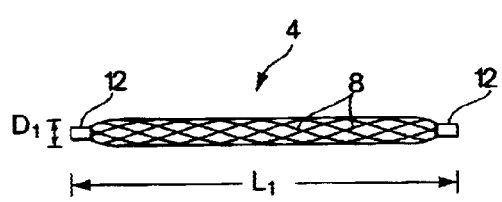 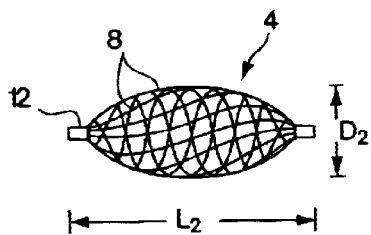
Fig. 10A    Fig. 10B
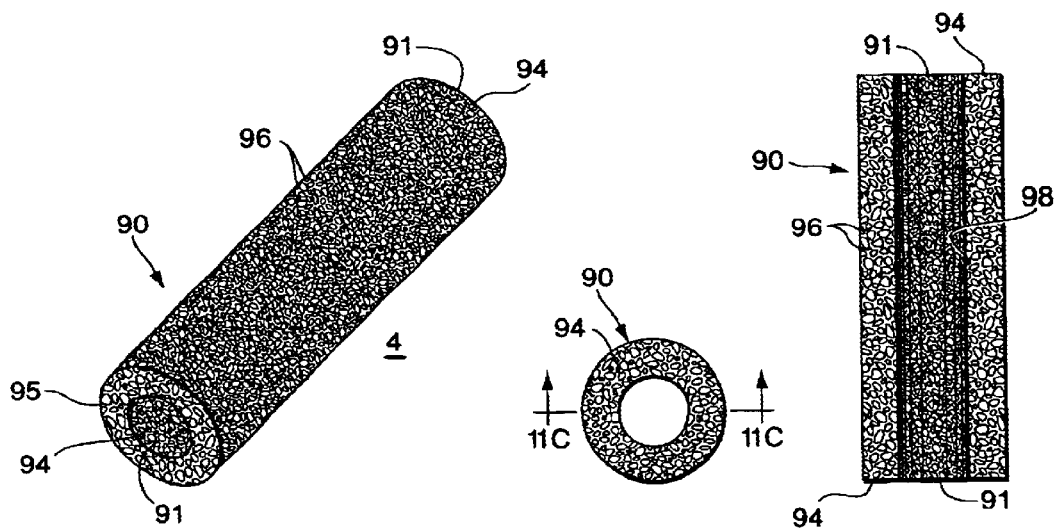
Fig. 11A    Fig. 11B    Fig. 11C

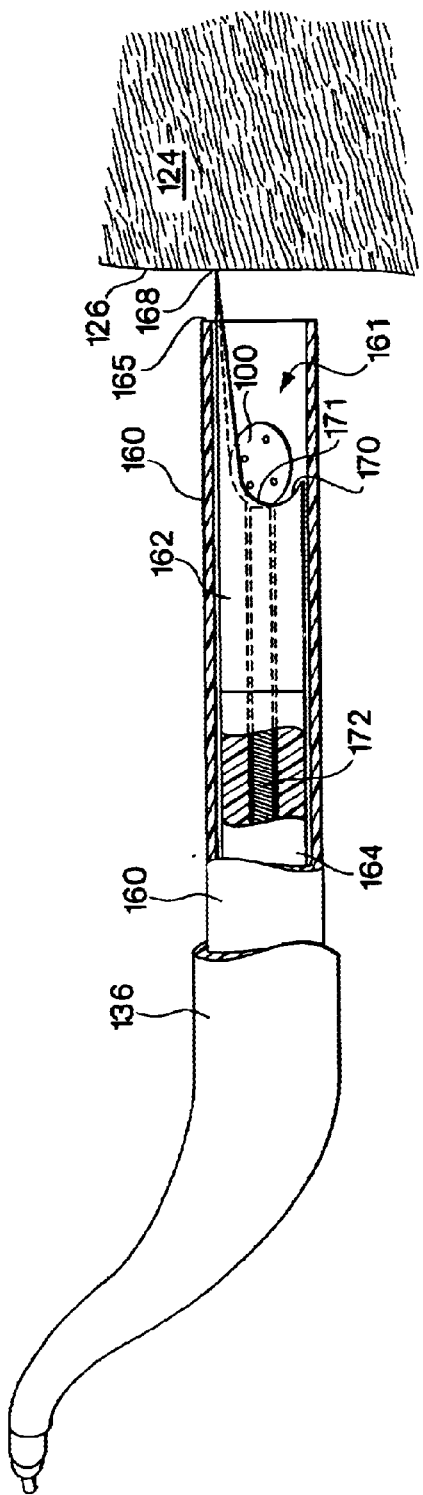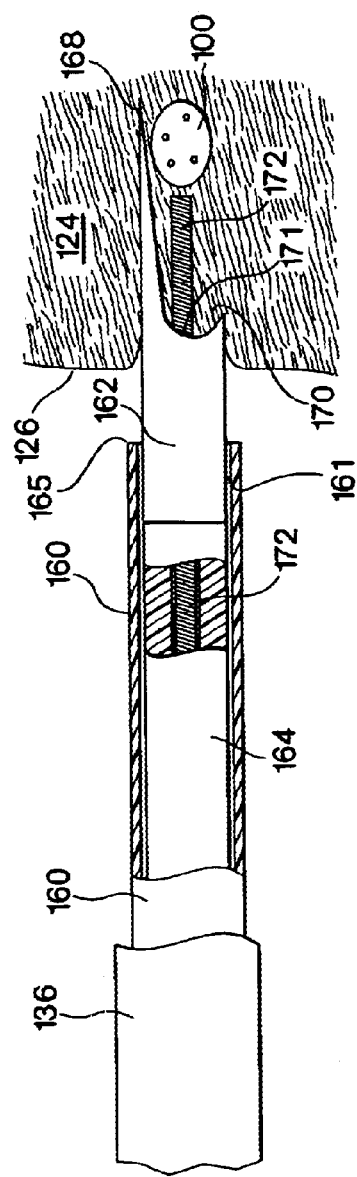
Fig. 17A
Fig. 17B

DEVICES AND METHODS FOR TREATING ISCHEMIA BY CREATING A FIBRIN PLUG

FIELD OF THE INVENTION

This invention relates to devices and methods for the treatment of ischemic tissue. In particular, the devices and methods initiate fibrin formation at sites in the ischemic region to promote angiogenesis and vessel recruitment, which revascularizes the ischemic tissue.

BACKGROUND OF THE INVENTION

Tissue becomes ischemic when it is deprived of adequate blood flow. Ischemia causes pain in the area of the affected tissue and, in the case of muscle tissue, can interrupt muscular function. Left untreated, ischemic tissue can become infarcted and permanently non-functioning. Ischemia can be caused by a blockage in the vascular system that prohibits oxygenated blood from reaching the affected tissue area. However, ischemic tissue can be revived to function normally despite the deprivation of oxygenated blood because ischemic tissue can remain in a hibernating state, preserving its viability for some time. Restoring blood flow to the ischemic region serves to revive the ischemic tissue. Although ischemia can occur in various regions of the body, often myocardial tissue of the heart is affected by ischemia. Frequently, the myocardium is deprived of oxygenated blood flow due to coronary artery disease and occlusion of the coronary artery, which normally provides blood to the myocardium. The ischemic tissue causes pain to the individual affected.

Treatment of myocardial ischemia has been addressed by several techniques designed to restore blood supply to the affected region. A conventional approach to treatment of ischemia has been to administer anticoagulants with the objective of increasing blood flow by dissolving thrombus or preventing formation of thrombus in the ischemic region.

Another conventional method of increasing blood flow to ischemic tissue of the myocardium is coronary artery bypass grafting (CABG). One type of CABG involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2, August 1965, pp. 181–189. Although researchers have reported varying degrees of success with various methods of piercing the myocardium to restore blood flow to the muscle (which has become known generally as transmyocardial revascularization or TMR), many have faced common problems such as closure of the created channels. Various techniques of perforating the muscle tissue to avoid closure have been reported by researchers. These techniques include piercing with a solid sharp tip wire, or coring with a hypodermic tube. Reportedly, many of these methods produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularization of the Heart by Laser", *Journal of Microsurgery*, Vol. 2, No. 4, June 1981, pp. 253–260. The laser was said to form channels in the tissue that were clean and made without tearing and trauma, suggesting that scarring does not occur and the channels are less likely to experience the closure that results from healing. U.S. Pat. No. 5,769,843 (Abela et al.) discloses creating laser-made TMR channels utilizing a catheter based system. Abela also discloses a magnetic navigation system to guide the catheter to the desired position within the heart. Aita U.S. Pat. Nos. 5,380,316 and 5,389,096 disclose another approach to a catheter based system for TMR.

Although there has been some published recognition of the desirability of performing TMR in a non-laser catheterization procedure, there does not appear to be evidence that such procedures have been put into practice. U.S. Pat. No. 5,429,144 (Wilk) discloses inserting an expandable implant within a preformed channel created within the myocardium for the purposes of creating blood flow into the tissue from the left ventricle.

Performing TMR by placing stents in the myocardium also is disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open channel in the myocardium through which blood enters from the ventricle and perfuses into the myocardium.

Angiogenesis, the growth of new blood vessels in tissue, has been the subject of increased study in recent years. Such blood vessel growth to provide new supplies of oxygenated blood to a region of tissue has the potential to remedy a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation*, 1998; 97:645–650.

Encouraging the initiation of naturally occurring angiogenic mechanisms within tissue such as the release of growth factors during coagulation and fibrin formation would be a desirable method of treating ischemic tissue. It has been recognized that coagulation proteases and regulatory acting during thrombus formation may initiate vascular proliferative responses. Robert S. Schlant (et al.), The Heart (1994).

A general object of the present invention is to initiate the body's injury response mechanisms, of which fibrin formation is a part, to treat ischemia. Treatment with the devices and methods of the present invention is considered to be contrary to conventional wisdom in view of the currently known methods of revascularization discussed above. Furthermore, the inventive devices and methods may provide more promising results because they utilize the body's own healing response as a mechanism of treatment.

SUMMARY OF THE INVENTION

The present invention provides devices and methods for promoting revascularization in tissue by initiating fibrin growth in that tissue. The devices and methods are intended to be useful in any tissue of the human body. However, the invention is most useful for treatment of ischemic tissue which has remained viable despite previous deprivation of adequate blood flow and would benefit from revascularization that occurs from the process of angiogenesis and vessel recruitment. Furthermore, because ischemic tissue has suffered injury, it may experience an injury response and be better conditioned to respond to the mechanisms that promote fibrin growth.

The invention utilizes the body's own healing process, the process of fibrin formation known as the coagulation cascade effect, to induce angiogenesis and recruitment of existing vessels to the ischemic region. The coagulation cascade is known to be initiated by injury or aggravation of the tissue. Aggravation may be mechanically or chemically induced. As a result of the tissue injury, collagen and connective tissue are exposed to blood. The injury activates platelets and, by either an intrinsic (factor XII is activated) or extrinsic (factor VII is activated) pathway, thrombin is produced. Thrombin is a catalyst that changes available fibrinogen into fibrin (a fibrous network formation). Fibrin helps to promote angiogenesis because its fibrous network provides a host structure for endothelial cells, which will form the new blood vessels to the ischemic area. Additionally, thrombin that has been produced and remains in the fibrin network serves to direct the endothelial cells to migrate and proliferate so that new vessels are formed to the fibrin area. The devices and methods of the present invention promote and sustain a localized area of fibrin growth, a fibrin plug, which releases growth factors helpful in recruiting existing adjacent vessels to the area of ischemic tissue, thereby supplying it with blood flow.

Both angiogenesis and recruitment of existing vessels are important mechanisms of revascularization that are initiated by practice of the present invention. Growth of new vessels to the fibrin plug area helps to expand and increase the density of the vascular bed. However, the new vessels may dissipate after the fibrin plug eventually is dissolved. Sustaining the fibrin growth permits existing vessels in adjacent tissue locations to be recruited, redirected, to the fibrin area to provide a sustained supply of oxygenated blood flow to the developing vascular bed. Growth factors released during the coagulation cascade reach adjacent vessels and redirect them to the site of fibrin formation. Capillaries and arterioles can be recruited to the ischemic region and serve to revascularize the tissue and supply the new vessels that have formed with blood.

The approach of promoting coagulation and fibrin growth to revascularize tissue is a departure from of conventional treatments that focus on increasing blood flow through existing pathways such as by thinning the blood and preventing thrombosis. Conventional treatments for ischemia have concentrated on preventing the clotting of blood so that blood may flow more freely to reach areas of reduced flow. Generally, thrombosis is considered to hamper blood flow and, therefore, to complicate conditions marked by reduced blood flow, such as ischemia. Conventional treatments to increase blood flow to a region include administration of anticoagulants, such as heparin, or fibrinolytic agents, which prevent the formation of fibrin. However, the present invention has resulted from the recognition that those very factors considered undesirable, such as fibrin and thrombus formation, can be used to treat ischemia because they initiate the growth of new blood vessels and the recruitment of existing vessels to the region. Angiogenesis can be initiated from fibrin formation, which results from the process of blood coagulation. Additionally, the presence of fibrin causes existing vessels in adjacent tissue to be redirected to the fibrin site.

The devices of the present invention are configured to promote fibrin and thrombus formation, which is contrary to conventional vascular implant device design. Commonly, devices that are implanted in an environment exposed to blood, such as in vascular applications, are configured, by their material, profile or by application of a coating, to be anti-thrombogenic. Conventional medical device design dictates that implant devices exposed to blood must be configured to resist thrombus formation so that blood flow around the device will not become restricted. The devices disclosed herein are configured to maximize thrombus formation in contrast to the prior art, which attempts to minimize thrombosis.

The present invention is intended to be useful in any tissue of the body that has become ischemic because of reduced blood flow to the region. For example, the legs commonly suffer from reduced blood flow that leads to ischemia of the muscle tissue in those regions. Also, the present invention is believed to provide particular benefit in the treatment of ischemic myocardial tissue of the heart. Restricted blood flow to the heart tissue is commonly caused by blocked coronary arteries. The ischemia that results from the reduced blood flow causes severe chest pain. The present invention provides treatment for ischemic myocardial tissue by promoting angiogenesis and vessel recruitment in the region to revascularize the ischemic tissue. It is emphasized, however, that the devices and methods herein disclosed are applicable to any area of body tissue in which it is desirable to promote revascularization. Furthermore, multiple devices can be implanted, or procedures performed, to initiate multiple sites of fibrin growth and vascularization activity in a region of tissue.

One embodiment of the invention comprises an device that is implanted into tissue and is configured to promote fibrin growth within the tissue. The implant device may be formed in a variety of configurations, but should comprise a structure or frame, flexible or rigid, having a region where fibrin growth may be fostered and held in association with the implant device. The fibrin retention region may be on the interior or exterior of the device. However, the device should be configured to permit communication between the associated fibrin and the surrounding tissue into which the device has been implanted. Blood, carrying agents of fibrin formation, must be permitted to flow to and from the fibrin network so that blood vessels will grow to the area of the fibrin plug. Additionally, the new and recruited blood vessels should have access to the fibrin growth so that permanent blood pathways to the ischemic area can be formed.

The formed fibrin should be securely associated with the implant device. If the fibrin is retained in an interior chamber of a device, openings between the interior and exterior of the device should be sized to be smaller than the size of the formed thrombus to capture the fibrin. If the device is configured to maintain fibrin on its exterior, the fibrin must be formed to the surface, adhered the device or retained in a matrix that can be adhered to the device, such as a thrombophilic coating.

The device and associated fibrin should be securely anchored in the tissue to prevent migration from the tissue and into the blood stream. It would be undesirable to have fibrin to enter the blood stream, becoming an emboli that may become lodged in an artery to a critical organ such as the brain or heart, possibly blocking blood flow to that organ. An implant device may tend to migrate when placed in active muscle tissue such as the myocardium. Cyclic contraction and relaxation of surrounding tissue can serve to push the implant out of its original implant location. Anchoring may, but need not, involve a dedicated component on the device such as a projection that claws into surrounding tissue. Anchoring also may be accomplished by configuring the device to have an overall shape that resists movement through the tissue. Furthermore, the method of delivery and placement of the device in the tissue may insure sufficient anchoring to prevent migration, without a specific anchor structure being associated with the device.

The devices may be configured to cause injury and irritation to surrounding tissue. Injury triggers a healing response in tissue leading to fibrin growth. Therefore, a device configured to cause injury while implanted helps to initiate and sustain the injury response and resulting coagulation, maximizing and maintaining the fibrin growth generated by the device. The device may be configured to irritate the tissue, either biologically or mechanically. A number of agents may be applied to the device to cause an adverse biological reaction in surrounding tissue or the device maybe formed of material that irritates tissue, such as a polymer. Mechanical irritation may be accomplished by configuring the device to have surfaces that irritate tissue, such as protrusions. The surfaces of the device serve to slightly injure the tissue during frictional contact between device and surrounding tissue. The frictional contact with the tissue occurs not only during implantation, but also, in the case of muscle tissue, constantly thereafter as the muscle relaxes and contracts.

The devices may be solid structures or may be hollow and define an interior chamber. Hollow structures may include, for example, mesh tubes, coils or capsules. Regardless of the exact configuration of a hollow device, if the interior chamber is intended to foster fibrin growth, it must be in communication with tissue that surrounds the implanted device. Agents of fibrin growth, such as thrombin, growth factors and endothelial cells should be free to flow between surrounding tissue and the fibrin growth. For example, pores or openings through the surface of the device should be present so that the substances that promote fibrin growth, and eventually new and recruited vessels, can flow between the interior chamber and exterior of the device.

The devices may be permanent or biodegradable. Also, the devices may have associated with them substances that promote fibrin formation or endothelial cell formation, such as growth factors. In the case of biodegradable implants, fibrin forming agents may be embedded in the biodegradable material so as to be released during the degradation of the material. The substance is released gradually into the surrounding tissue as the material degrades to promote fibrin growth. In the case of permanent implants, a growth factor or fibrin producing substance may be applied by coating the surfaces of the device with the substance or with a composition that serves to host the substance. The substance is released from the coating of the device over time as the coating dissolves or as blood gradually carries it away from the coating matrix.

Another method of enhancing the angiogenic effect of the implant is by associating with the implant a thrombus (advanced fibrin growth) formed from blood previously removed from the body. The thrombus may be formed within the interior chamber of a hollow device ex vivo or preformed ex vivo first, then placed into the interior prior to or after implantation. In the case of a solid device, the fibrin may be permitted to form around the exterior of the device ex vivo before it is implanted in tissue. The formed thrombus may hasten revascularization in the subject tissue by providing a ready made completed fibrin network into which growth factors and endothelial cells may be attracted. Also, the formed thrombus could be preloaded with growth factors or other agents, thereby serving as a natural, biodegradable host network for the angiogenic agents.

A thrombophilic substance also may be associated with the device prior to implantation to increase the angiogenic effect of the device. The thrombophilic substance collects and retains blood present in the tissue into which the device has been implanted. The retained blood will tend to coagulate in vivo, beginning the coagulation cascade, which leads to the formation of a fibrin plug. The coagulation promoted by the thrombophilic substance tends to maximize the fibrin growth resulting from placement of the device, which enhances the revascularative effect of the implant.

An alternative method of the invention involves placing a thrombus or fibrin producing substance, or a thrombophilic substance, directly into the tissue to be treated without an associated device. As explained above, the presence of such substances in tissue, with blood present, enhances fibrin production and its associated revasculative effect. Therefore, as an alternative to implanting a device, fibrin producing substances alone may be administered to induce fibrin growth.

It is an object of the present invention to provide devices and methods to stimulate fibrin growth and its associated revascularative effect.

It is another object of the invention to provide a reliable treatment for ischemia whereby ischemic tissue is revascularized by new and recruited vessels.

It is another object of the invention to provide a method of treating ischemia that utilizes the body's own physiological responses by fostering fibrin growth in the ischemic tissue.

It is another object of the invention to provide a method of promoting angiogenesis in tissue.

It is another object of the invention to provide treatment for ischemia that is safe and reliable for the patient.

It is another object of the invention to provide methods and devices for revascularizing myocardial tissue by creating a fibrin plug in an ischemic region.

It is another object of the invention to provide an implant device configured to promote thrombus formation.

BRIEF DESCRIPTION OF THE DRAWINGS

The foregoing and other objects and advantages of the invention will be appreciated more fully from the following further description thereof, with reference to the accompanying diagramatic drawings wherein:

FIG. 10A is a side view of an expandable implant device in an elongate, low profile configuration;

FIG. 10B is a side view of an expandable implant device in its short, large profile configuration;

FIG. 11A is a isometric view of an open cell implant device;

FIG. 11B is a end view and a longitudinal cross-sectional view of an open cell implant device;

FIG. 11C is a cross sectional view of the open cell implant device of FIG. 11B taken along the line 11C—11C;

FIG. 17A is a side view and partial cut-away view of a delivery device delivering a pellet implant device to a tissue location;

FIG. 17B is a side view and partial cut away view of a delivery device delivering an implant device to a tissue location;

DESCRIPTION OF THE ILLUSTRATIVE EMBODIMENTS

Figure 1:
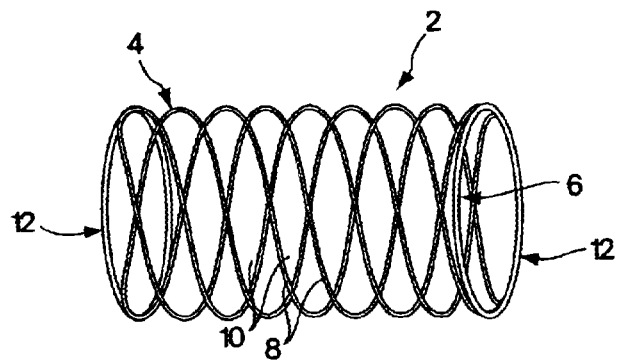
FIG. 1 is a side view of an implant device comprising a mesh tube frame.

FIG. 1 is a general representation of an implant device 2 that is configured to promote fibrin growth when implanted in tissue. The implant device may comprise a tubular structure such as the mesh tube 4 shown in FIG. 1. The tube defines an interior chamber 6, which may be considered a fibrin retention region in that it defines an area where fibrin may grow and be associated with the device. The cavity defined by the interior chamber 6 collects blood available in the tissue into which the device has been implanted, the collected blood tends to coagulate, beginning the coagulation cascade, which leads to fibrin growth and ultimately angiogenesis in the subject tissue. Thus, an implant device 2 such as a mesh tube 4 provides a frame in which blood pooling and coagulation and the resulting fibrin growth can be fostered. Tube 4 provides anchoring capability by the virtue of its wide openings 10, which permit surrounding tissue to herniate into the interior chamber of the stent, engaging elongate members 8 to hold the device in place.

Also important in the promotion of fibrin growth is the existence of communication pathways between the new fibrin growth and surrounding tissue and blood. It is important that substances released from the tissue and blood, such as growth factors, reach the fibrin retention region of the device to enhance coagulation and fibrin formation. Also, growth factors and thrombin that are held in the formed thrombin should be able to flow into the tissue that surrounds the device. In the case of the mesh tube 4 shown in FIG. 1, interwoven elongate members 8 define a plurality of openings 10 into the interior chamber 6 of the tubular structure. The open mesh pattern defined by the members 8 and openings 10 supports surrounding tissue when implanted so that it does not collapse into the interior chamber 6 of the device. Open ends 12 also permit communication between the interior chamber of the device and surrounding tissue.

Figure 2:
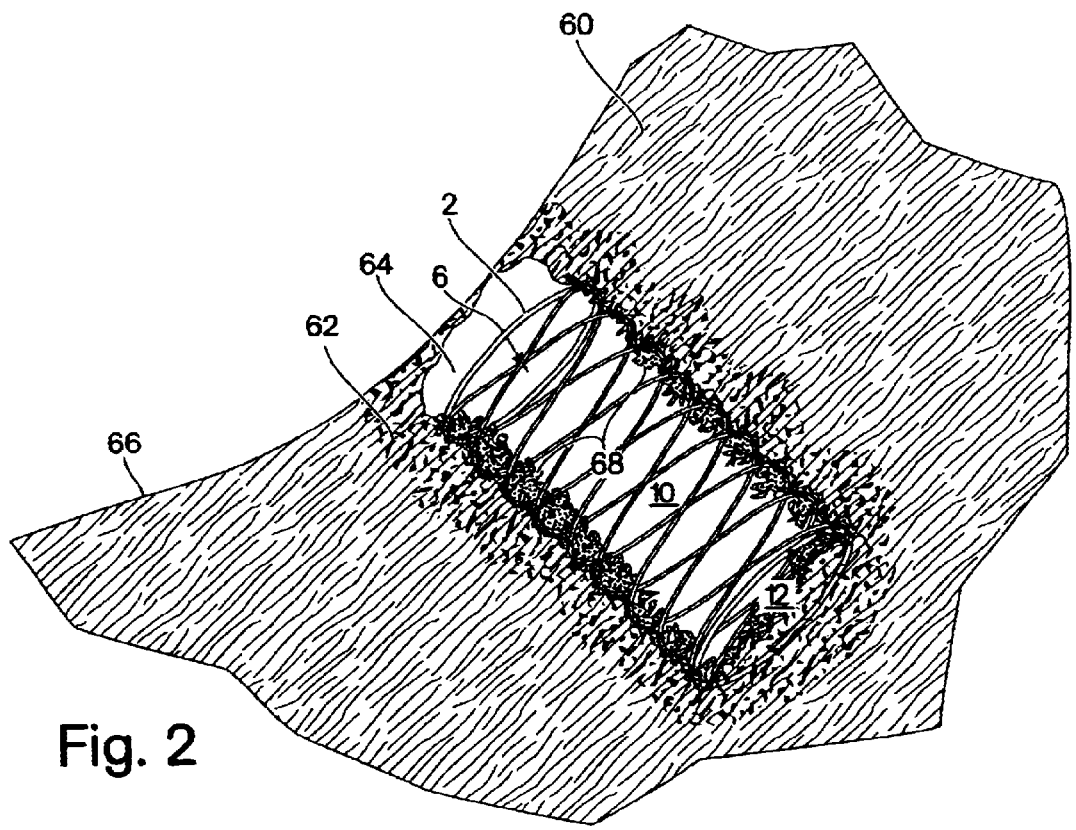
FIG. 2 is a diagramatic illustration of an implant device placed in tissue.

FIG. 2 shows a representative device 2 of the present invention implanted in tissue 60. The device 2 comprises a frame, such as the mesh tube structure 4. Though the mesh tube embodiment 4 is depicted in the drawings accompanying this explanation of the interactions between the implant devices and fibrin growth, it should be understood that the mesh tube embodiment is shown only as one example of a functional device configuration. The inventive devices may have a variety of configurations of which some illustrative examples are discussed below. Any of these device configurations could be substituted for the implant device 2 shown in FIGS. 2–5. However, as mentioned above, it is important that the device 2 be configured to have an area in, on or around the device that encourages the fibrin to grow and become associated with the device: a fibrin retention region. In the example of a hollow tube frame device, the fibrin retention region comprises the interior chamber 6 of the device.

A channel may, but need not be, pre-formed into the tissue prior to delivery of the implant device 2. Techniques for forming channels into tissue are known in the art and include: piercing by needle, coring by hypodermic tubing and ablation by mechanical means or by laser or radio frequency energy. After forming a channel into the tissue a device may be installed to promote fibrin growth. However, it is preferable to use a delivery device and method that simultaneously penetrates and inserts the device into the tissue. The penetration by the implant device may be facilitated by the piercing capability of the associated delivery device as discussed below. The piercing of the delivery device and advancement of the implant device momentarily create a cavity 64 in the tissue into which the implant is placed. Immediately following insertion the tissue attempts to return to its original position and surrounds the implant.

When the device 2 is placed within the tissue, an area of irritated tissue 62 is created by the frictional contact of the device sliding into the area. The irritated tissue 62 immediately surrounding the implanted device is further irritated as it herniates through openings 10 and end openings 12 of the device. Each herniation point 68 protrudes into the interior chamber 6 of the device as the tissue attempts to recoil to its original position prior to creation of the cavity 64 and implantation of the device 2. In the case of muscle tissue, further irritation occurs from ongoing frictional contact with the device during relative movement between the device and tissue as occurs during flexure and relaxation of the muscle tissue. Irritation of the tissue is beneficial because it initiates and sustains an injury response, initiating the coagulation cascade, which leads to fibrin growth. Maintaining and sustaining the localized fibrin growth encourages recruitment of adjacent existing vessels to the fibrin plug site.

The device may be implanted at any depth within the tissue, but should be securely implanted so that it does not migrate out of the tissue. The device may be completely submerged in the tissue, flush with the surface 66 of the tissue or exposed and protruding from the surface. However, the device should not be left protruding from the tissue if its presence would interfere with the function of other body organs or passageways. Ideally, the device is implanted at a depth level in ischemic tissue where the highest vascular activity is likely to occur. For example, in myocardial tissue of the heart, the area closest to the endocardium is known to have greater vessel density than the area of the myocardium adjacent the epicardium. Therefore, vessel growth is considered to be more active near the endocardium. Consequently, that area is believed to benefit more prominently from the angiogenic effect of a localized area of fibrin growth or formation of a fibrin plug.

In the context of treating ischemic myocardial tissue, FIG. 2 depicts a device 2 implanted near the endocardial surface 66 of the myocardium 60. As mentioned above, the device may, but need not be implanted at a depth below the surface of the tissue. Implanting the device below the surface 66 causes tissue to recoil around all sides of the device, helping to anchor the device so that neither the device nor the associated fibrin migrates out of the tissue and into the blood stream.

Blood present in the subject tissue aides in beginning the coagulation cascade, which results in fibrin growth. Ischemic tissue that is hibernating and still viable has some blood present, which can interact with the device 2 to begin the coagulation cascade. The hollow interior chamber 6 of the device 2, shown in FIG. 2, provides a depot or retention region for fibrin growth. The device provides a frame structure that holds back surrounding tissue and maintains an open cavity 64, defined by the interior chamber 6 of the device. The interior chamber 6 serves as an adequate fibrin retention region because it permits blood present in the tissue to pool in the open cavity 64 where it has an opportunity to coagulate and form into fibrin.

Figure 3:
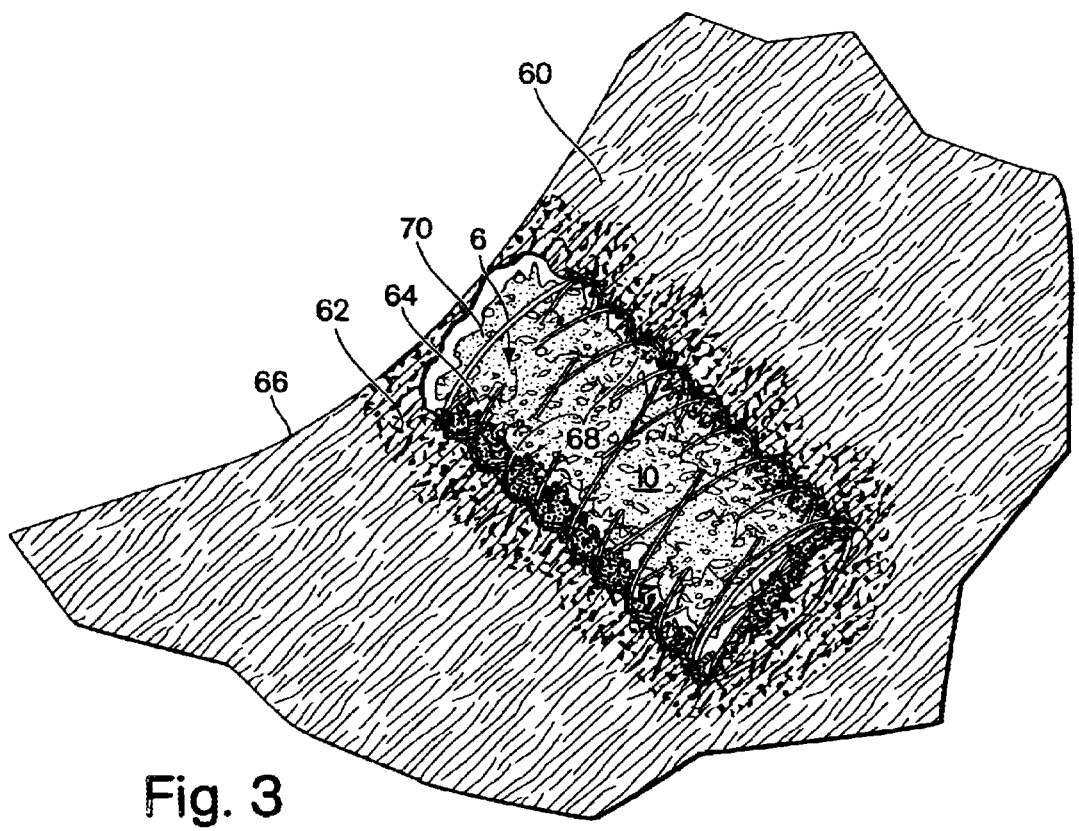
FIG. 3 is a diagramatic illustration of an implant device placed in tissue after fibrin has begun to form.
Figure 4:
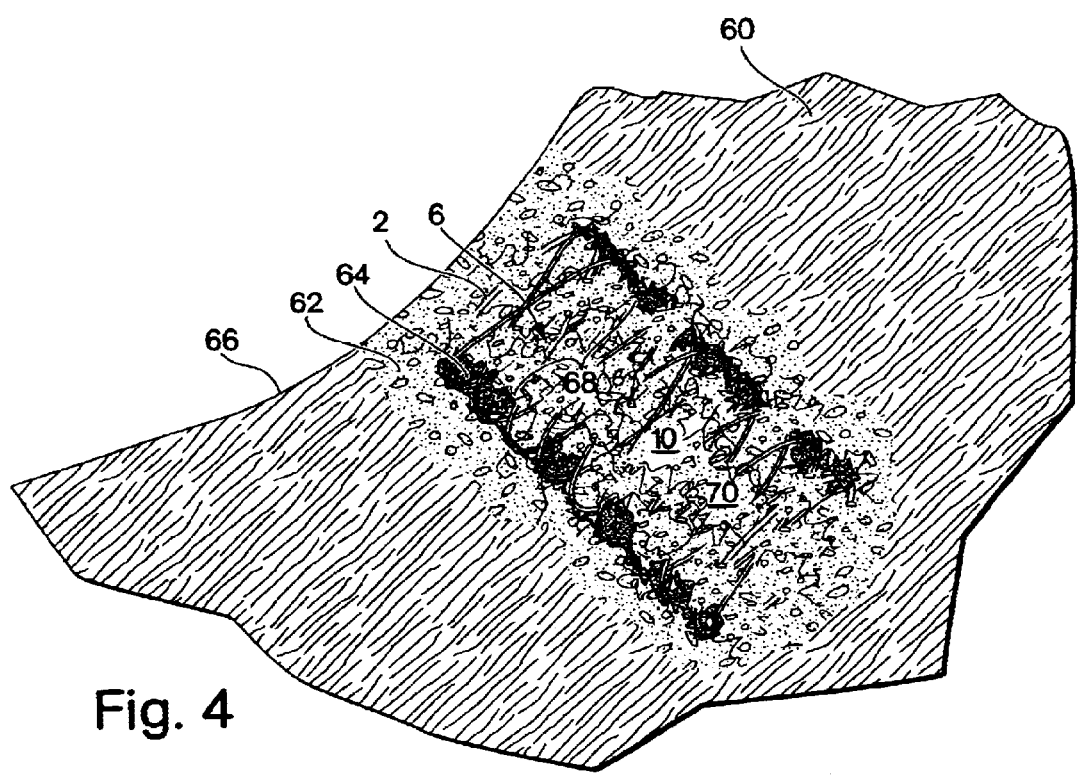
FIG. 4 is a diagramatic illustration of an implant device in tissue, after advanced fibrin formation has occurred.

As shown in FIG. 3, fibrin 70 begins to develop in the interior chamber 6 of the device 2 as the coagulation cascade proceeds. The presence of openings 10 throughout the device permits naturally occurring agents of fibrin formation (platelets, growth factors, thrombin and fibrinogen) to flow with the available blood into the interior chamber 6 of the device where they will pool and begin to form the fibrin plug 70. Additionally, the agents of fibrin formation act on the area of irritated tissue 62 to form fibrin in the tissue that surrounds the implanted device. As the fibrin formation progresses, the amount of fibrin expands to occupy the area defined by the interior chamber 6 of the device, filling the cavity 64 that was created in the tissue 60 by the implantation of the device as is shown in FIG. 4. Preferably, the amount of fibrin formation at the fibrin retention region is maximized to correspondingly maximize the resulting angiogenesis and vessel recruitment in the region. Eventually, herniation points 68 form fibrin linking the fibrin 70 formed inside the device frame and the fibrin formed in the area of irritated tissue 62 surrounding the device.

Figure 5:
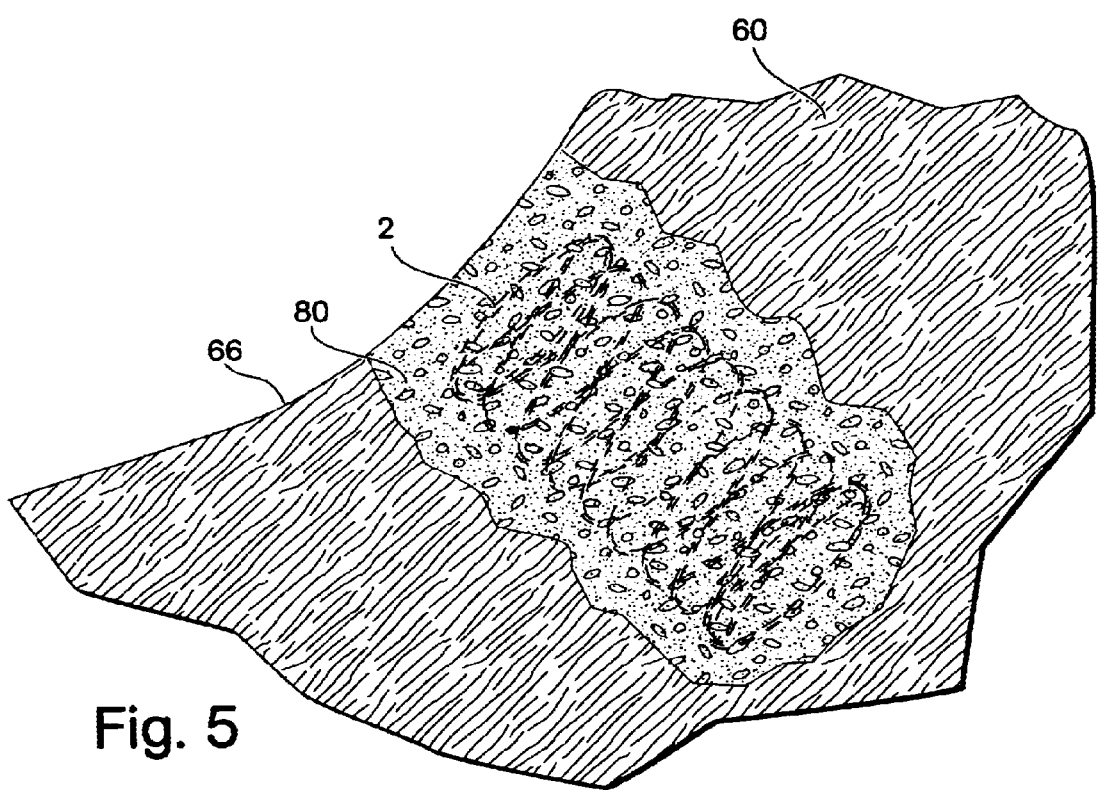
FIG. 5 is a diagramatic illustration of a formed fibrin plug.

As shown in FIG. 5, ultimately a fibrin plug 80 is completely formed in the area of tissue affected by the implant device 2 (shown in phantom). The fibrin plug promotes revascularization in the tissue, for several reasons. The fibrin plug provides a fibrous network, which serves as a host structure for endothelial cells that form new blood vessels in the ischemic area. The fibrin network also hosts thrombin that is produced during the coagulation cascade, which serves to incite the endothelial cells to migrate and proliferate to form the new blood vessels. The thrombin also encourages the release of various growth factors from surrounding cells, which help promote the growth of new vessels and also serve to recruit existing vessels from adjacent tissue areas, redirecting them to the fibrin plug site.

The revascularization that results from the fibrin growth primarily occurs by two mechanisms: new vessel formation, and recruitment of existing vessels from adjacent tissue. As explained above new vessels are generated by the presence of thrombus, endothelial cells and growth factors. The presence of fibrin and growth factors also serve to redirect existing vessels to the site of the fibrin. Arterioles and capillaries may be recruited. Physiologically, the body recruits vessels to the fibrin site for the purpose of breaking down the fibrin with enzymes and macrophages carried in the blood. Though ultimately the fibrin will be broken down in the final stages of the healing process, the ultimate. objective of revascularizing the ischemic region will have been achieved by the arrival of new and recruited vessels, restoring oxygenated blood flow to the region. Preferably the fibrin plug is maintained a sufficient period of time to permit, existing vessels to reach the site. It is expected that, after the vessels have reached the fibrin plug, the subject tissue will tend to remain revascularized, even after the fibrin is dissolved and scar tissue is left in its place. Any adverse effect that may be experienced by the presence of scar tissue in the location of the fibrin plug is outweighed by the overall benefit provided by revascularization of the region.

Several fibrin plugs may be formed in a given area of ischemic tissue, in relatively close proximity to each other, to increase the resulting vascularization effect. By way of example, the implants may define a width of approximately 1–2 mm and a length corresponding to somewhat less than the thickness of the tissue into which it is implanted. In the case of myocardial tissue, an implant length of approximately 6 mm is believed to be an adequate size to achieve the desired angiogenic effect. Though increasing the size of the implant may result in greater fibrin growth, the quantity and size of the implant devices should not be so large that the movement of the subject muscle tissue is adversely affected. It is expected that implants having a 2 mm wide profile would serve an area of ischemic tissue of approximately one square centimeter to adequately promote revascularization throughout the surrounding region of tissue yet avoid interfering with the function of the muscle. Device flexibility also affects the tissue's function after placement of a plurality of devices. More flexible devices move more freely with surrounding tissue and, therefore, affect its function less prominently. However, it is recognized that that some resistance to tissue movement by the device is desirable to help irritate the tissue and cause an injury response. The devices herein described are configured to be flexible, so as not to impede muscle function, yet provide sufficient fortitude to sustain a fibrin retention region and to irritate the tissue. For example, the tubular devices described herein may be constructed from 316 stainless steel filament on the order of approximately 0.001"–0.002" in diameter.

Figure 6:
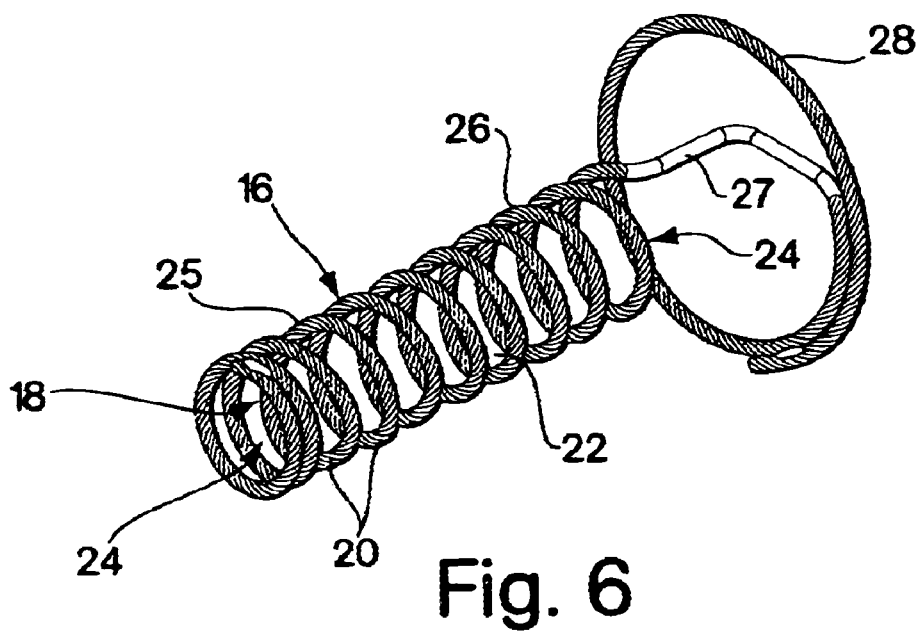
FIG. 6 is an isometric view of an implant device comprising a coil frame and anchor mechanism.

An alternative tubular implant device, formed as a helical coil 16, is shown in FIG. 6. Like the mesh tube 4, the coil device has an interior chamber 18, which is defined by the individual turns 20 of the coil. The helical coil 16 defines a frame, which holds back surrounding tissue so that blood may pool in the interior chamber, coagulate and become fibrin. Spaces 22 between individual turns of the coil permit communication between the interior chamber 18, where fibrin will grow and the blood and tissue that surround the device. Open ends 24 also permit communication between the interior chamber 18 and surrounding tissue. The coils 16 may also have a tail 28 configured to resist excessive penetration of the device into the subject tissue so that the overall depth that the device is implanted in the tissue is controlled. The tail 28 may be configured in a variety of forms. The example of a tail shown in FIG. 6 comprises a single broad coil joined to the main body 25 of the device by an extension 27, which may be a continuation of the coil 16. When the device is implanted in tissue, the broad coil of the tail is positioned to be flush with the surface of the tissue. The broad coil tail distributes the migratory forces experienced by the device over a broad area of tissue surface. The tail resists penetration of tissue surface thereby preventing migration of the device further into the tissue. Additionally, filament 26 from which the coil is formed may be a solid material or may, itself, be a coil spring structure having a plurality of openings between turns of the coil, which serve to permit herniation of surrounding tissue into the coil for anchoring capability.

Figure 7:
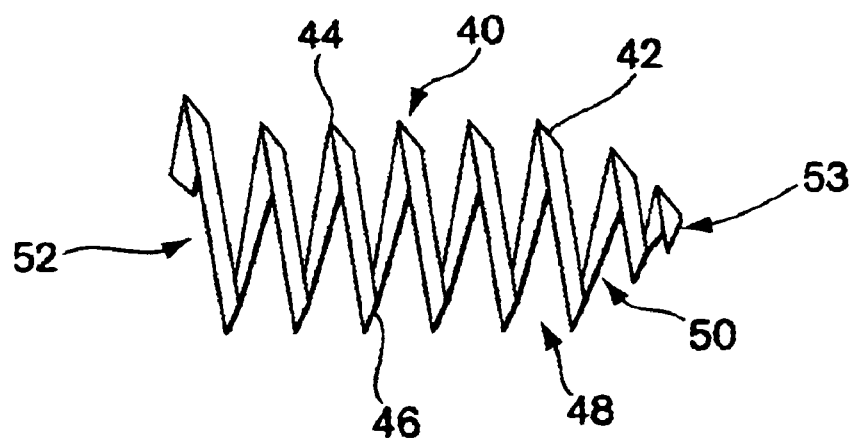
FIG. 7 is a side view of an implant device comprising a canted coil.

FIG. 7 shows yet another alternate embodiment of a tubular frame device. The canted coil device 40 is formed from a filament 42 of rectangular cross-section such as a strand of flat wire. The coil is formed so that the major cross-sectional axis of the rectangular wire is oriented at an acute angle to the longitudinal axis of the coil. The orientation gives each turn 46 of the coil a projecting edge 44, which tends to claw into tissue to serve as an anchoring mechanism for the device. As with the coil shown in FIG. 6, fibrin growth is promoted within the interior chamber 50, which serves as the fibrin retention region of the canted coil 40. Also, communication between the fibrin and surrounding tissue occurs through open ends 52 and spaces 48 between individual turns 46 of the coil. An example of a canted coil device is disclosed in U.S. application Ser. No. 09/073,118.

Figure 8:
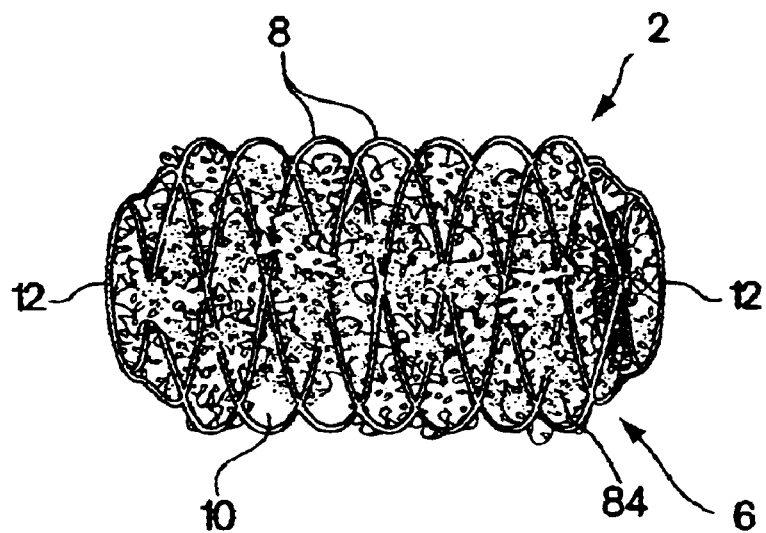
FIG. 8 is a side view of an implant device having associated with it a thrombus.

The inventive devices and methods may be modified to intensify or expedite fibrin formation. FIG. 8 shows an implant device 2 having formed fibrin, a thrombus 84 associated with it prior to implantation into tissue. The thrombus 84, may be formed ex vivo while in contact with the device 2, or may be permitted to form ex vivo then, later either ex vivo or in vivo, associated with a fibrin retention region of the device such as the interior chamber 6 of the hollow tube example shown in FIG. 8.

In FIG. 8, the fibrin 84 is shown occupying an area of the interior chamber 6 of the device 2 and surrounds some of the interwoven elongate members 8. The thrombus may be associated with the device in this configuration by removing a small quantity of blood from the patient prior to implantation of the device, associating the blood with the fibrin retention region of the device, placing the device and blood in an environment where the blood remains in or on the fibrin retention region of the device and in which the coagulation cascade may take place. As the cascade progresses, blood becomes formed fibrin or a thrombus 84 that is formed around a component of the device and becomes associated with the device. The fibrin retention region may constitute any area of the device capable of holding fibrin. Therefore, the fibrin may be formed around the exterior surface of a device or on only a portion of a surface of the device.

Alternatively, a thrombus 84 may be permitted to form apart from the device 2 from blood removed from the body. After the thrombus 84 is formed, it can be associated with the device such as. by placement in the interior chamber 6 of the tubular frame of device 2 prior to or after implantation in the body. The thrombus 84 should be securely associated with the device so that it does not become disassociated from the device and surrounding tissue after implantation. If the thrombus were to enter the blood stream it may later block blood flow to critical organs. To secure the thrombus 84, it may be placed in a gel solution or other adhesive, which may then be associated with the device adhering to its surfaces.

In the case of devices having an interior chamber 6, such as a tubular embodiment shown in FIG. 8, the open ends 12 may be configured to be a reduced diameter or closed so that the thrombus 84 is caged within the frame of the device despite not being adhered to any particular surface of the device. The coil embodiments of FIGS. 6 and 7 may have end coils wrapped more tightly and defining a smaller diameter than the coils of the body. The small diameter end coils should be sized to define a diameter smaller than the profile of the formed thrombus to be contained in the implant device. The flexible coils can be temporarily elastically deformed to permit loading of the thrombus into the interior chamber of the device. The small diameter end coils serve to retain the thrombus. An example of a reduced diameter end coil configuration is represented by the proximal coil 53 of coil implant device 40 in FIG. 7.

A device 2 preloaded with a formed thrombus 84 expedites the angiogenic effect that fibrin formation creates in tissue. The pre-formed thrombus 84 immediately begins serving as a host network for endothelial cells, growth factors and thrombin, all of which serve to promote further fibrin growth and ultimately the growth of new blood vessels to the site of the implant.

Figure 9:
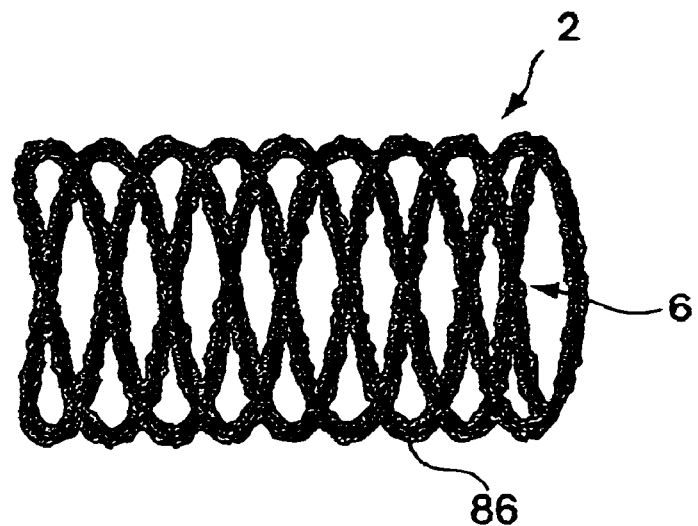
FIG. 9 is a side view of an implant device coated with a substance.

Another aspect of the invention provides for enhancing fibrin growth by coating the device 2 with a fibrin growth enhancing substance 86. As shown in FIG. 9, the coating 86 may comprise a polymer and should contain substances such as growth factors or thrombin which aid in the coagulation cascade process. The coating material 86 may be applied over the entire frame of the device 2 or may be applied only to certain areas, such as the surfaces of the interior chamber 6, or anywhere on the device that is intended to be the fibrin retention region. A benefit of coating the device with fibrin producing substances is that the substances will be released gradually, in a sustained fashion, within the immediate area where the fibrin plug formation is intended. The release of these substances helps to sustain the fibrin growth, giving new and recruited vessels time to develop to revascularize the area of tissue.

The device 2 also may have associated with it a thrombophilic substance to aid in fibrin formation. A thrombophilic substance absorbs and holds blood that comes into contact with it. Blood suspended in the swollen thrombophilic material is in an ideal environment for fibrin formation because it is maintained stagnant, yet communication pathways with surrounding tissue and blood remain open. Therefore, a device coated with a thrombophilic substance may provide an enhanced mechanism of creating fibrin. Hydrogel is an example of a thrombophilic substance that may be coated onto the device prior to implantation.

All devices of the present invention may be formed from biodegradable materials without adversely affecting their function. Biodegradable devices degrade over time so that a permanent implant does not remain in the body. The objective of forming a fibrin plug can be achieved by a temporary frame structure, that provides a host network to hold the elements of fibrin formation during the cascade process. However, after the fibrin has formed and new vessels have grown to serve the fibrin plug, the implant device is not needed. The device dissolves, leaving in place the formed fibrin network. The biodegradable material should be formulated to sustain its structure at least long enough for fibrin formation to begin. After it forms, the fibrin becomes a host structure for agents of further fibrin formation and for angiogenesis and vessel recruitment. Another benefit of a biodegradable device is that the biodegradable material may be impregnated with a fibrin producing substance such as a growth factor, which will be gradually released into the subject tissue as the implant degrades, helping to sustain the fibrin growth.

The fibrin promoting devices shown in FIGS. 1–7 may be formed of a variety of materials. Bioabsorbable materials may include L-Lactide polymers. Examples of biostable materials include implantable polymers, stainless steel, or nickel titanium alloys.

An implant device according to the present invention may incorporate any combination of the above described features. An example of a device configured to expedite fibrin formation according to the above concepts may include a frame structure such as a mesh tube 4 formed from a biodegradable material that has been impregnated with a fibrin producing substance such as a growth factor and having associated with the fibrin retention region, either a thrombophilic substance or a preformed thrombus. A device so configured promotes fibrin growth in several ways. The frame promotes blood pooling within its interior chamber and serves to irritate surrounding tissue by its frictional contact with the tissue. A biodegradable frame further promotes fibrin by the gradual and sustained release of growth factors, which encourage fibrin formation and vessel development. A preformed thrombus not only serves to promote angiogenesis more quickly after implantation, but also encourages further fibrin growth by providing a ready made frame structure in which the agents of fibrin formation may reside. The preformed thrombus also hastens the response of nearby vessels that are recruited to the thrombus site. A thrombophilic substance attracts and holds blood to help initiate coagulation.

The devices may be delivered and implanted in a single configuration of constant profile. Alternatively, the devices may be configured to be expandable from a reduced profile, delivery configuration to an expanded, larger profile configuration. Configuring the devices to be expandable may facilitate delivery, if the delivery method requires navigation through a confined bodily approach path. Also, a device that is expanded in situ may be anchored more securely as frictional contact with surrounding tissue is increased and tissue is forced to herniate into openings or cavities of the device. An expandable device may obviate the need for a distinct anchoring mechanism, if it the expanded configuration securely positions the device in the intended tissue location.

An example of an expandable implant device is shown in FIGS. 10A–10B. The interwoven arrangement of the interconnecting elongate members 8 of mesh tube 4 permit the tube to be moved from a smaller diameter D1, longer configuration L1 (FIG. 10A) to a larger diameter D2, shorter configuration L2 (FIG. 10B). The members are free to slide against each other and are secured only at ends 12 such as by soldering. The configuration may be expanded, after delivery to the tissue, by applying through the delivery device a longitudinal force on the implant device 4 to reduce its length. The coils shown in FIGS. 6 and 7 may also be configured to be expandable from a low profile configuration to a larger profile configuration. The coils 16 and 40 undergo a change in diameter with a corresponding change in length and number of turns in the coil. However, it is emphasized that expandability of the device is not essential to the function of the invention and the devices may be delivered and implanted in a single configuration.

Because the coagulation cascade and resulting fibrin formation are a result of tissue irritation and injury, it is useful for the devices of the present invention to be configured to cause some irritation and injury to the tissue into which they are implanted. Not only do the penetration and insertion of the device into tissue cause irritation and injury, but also the continued presence of the device within the tissue that has recovered to surround the device tends to be a sustained source of injury. In the case of muscle tissue, which relaxes and contracts regularly, frictional contact with the device surface is created, which continually irritates or injures the tissue. The ongoing injury sustains the tissue's injury response and its fibrin promoting effect.

The benefits of inducing a tissue injury response can be further enhanced by increasing the device surfaces that engage and injure the tissue. To enhance tissue injury, the number of individual irritation or nucleation points the device creates with the tissue should be maximized. This can be accomplished by adding projections to the exterior surface of a device or by roughening the surfaces of the device that will be in contact with tissue when it is implanted. Another approach to increasing the number of irritation points is shown on coil 16 in FIG. 6. A filament 26 formed from a coil, as opposed to a solid wire, provides more openings into which the tissue may herniate and thus create more contact points with the tissue on each individual turn of the coil.

Another approach to providing a device configured to meet the objectives of the present invention is to utilize an open cell structure material, such as foam, in the device. By way of example, a foam tube 90 is shown in FIGS. 11A–11C. Any expanded polymer material such as foam can provide an open cell structure frame that is suitable to serve as a fibrin promoting implant device. Each open cell 96 provides a cavity that can accept blood present in the surrounding tissue, permitting it to pool, stagnate and eventually coagulate. Therefore, the device material, itself, provides a fibrin retention region because each open cell provides a cavity where blood may pool. As shown in FIGS. 11A and 11C the open cell structure may be provided with an interior 91, which not only provides additional space for a fibrin retention region, but also provides a structure that may be more easily retained on a delivery device, such as those discussed in detail below. However, though a tubular shaped device is shown in FIGS. 11A–11C, an open cell material device may be configured in a variety of ways, even a solid, because the device material itself comprises the fibrin retention region.

Blood that pools and coagulates in the individual cells 96 of the open cell material remains in communication with blood and tissue surrounding the device. As the coagulation cascade progresses, fibrin proliferates in the open cell structure of the device. The porous material also permits transfer of blood and other substances through the open cell material to the interior 91, if the device is so configured. The porous and rough surface of the material also serves to interact with surrounding tissue so that the tissue becomes irritated. Surrounding tissue grips into pores 96 to prevent migration of the device.

Figure 12A:
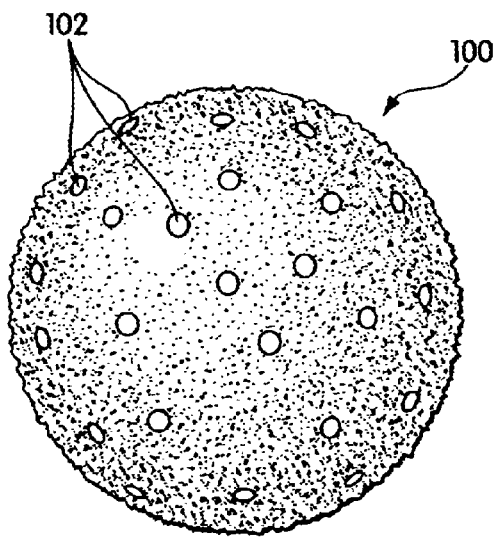
FIG. 12A is a side view of a pellet implant device.
Figure 12B:
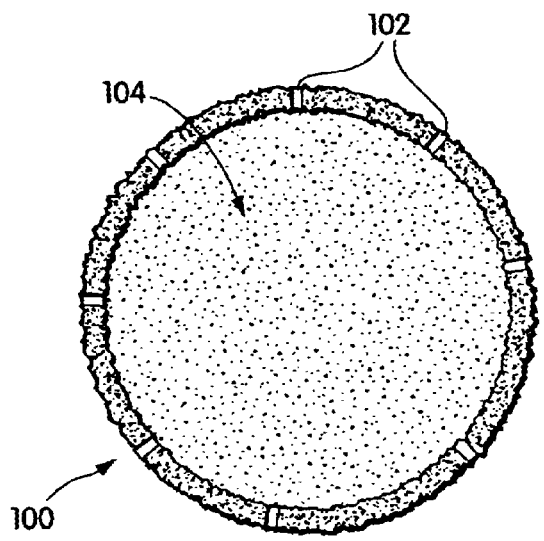
FIG. 12B is a cross-sectional view of the pellet implant device of FIG. 12A taken along the line 12B—12B.

Though the exemplary implant devices discussed above have been described as tubular frame configurations, other implant configurations can be equally as effective. Another alternative configuration is that of a pellet 100 shown in FIGS. 12a and 12b. The pellet may be made from a material such as a biostable or bioabsorbable polymer. Alternatively, the pellet may be formed entirely of a natural biological substance that is inert and formable, similar to a pill. As with the previous embodiments the pellet provides a frame, which is configured to have a fibrin retention region that fosters fibrin growth. The pellet could be shaped in a variety of configurations; however, for illustration purposes it is shown as having a generally spherical shape in the FIGS. 12A–13.

The pellet may be solid or may be configured, during or after formation, to be hollow with an interior chamber 104 to form a capsule. The fibrin retention region may comprise the exterior surface of a solid pellet, the interior chamber of a hollow pellet, or the pores of a porous pellet. The interior chamber 104 or the pellet material, if porous, may be filled with a fibrin producing substance, such as a growth factor, prior to implantation into tissue. Openings 102 can be made through the surface 112 of the hollow pellet to permit an exchange of fibrin producing agents and blood between the interior chamber 104 and surrounding tissue. A suitable pellet size may be on the order of 1–2 mm in diameter. Alternatively, very small pellets, or microspheres may be implanted. Microspheres are generally on the order of several microns in diameter and are formed from a porous material such as a polymer or natural substance. Generally, a plurality of microspheres are implanted in a given area of tissue to increase the overall therapeutic effect for any given area. The area immediately surrounding and between the microspheres also may serve to host fibrin growth.

Figure 13:
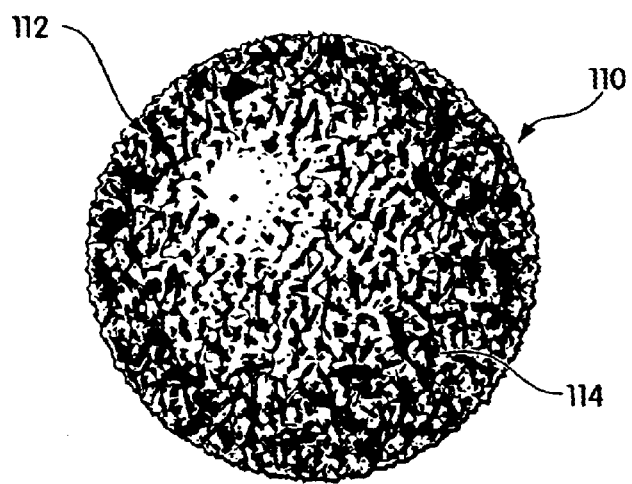
FIG. 13 is a side view of a pellet implant device.

As mentioned above, devices of the present invention may be configured as a solid. If the material from which they are formed is not porous, the exterior surface of the device can provide a fibrin retention region which fibrin growth is promoted. FIG. 13 shows a pellet 110 of solid material. As with the previously described devices, the material may be biostable or bioabsorbable. The pellet may be made from any material that is not toxic to the body. A rough outer surface 112 encourages pooling of small amounts of blood in small crevices 114 that cover the surface. Blood also pools in pockets that may exist between the crevices and surrounding tissue. The collected blood coagulates and becomes fibrin, which ultimately surrounds the device. In this embodiment, it is the outer surface 112 that serves as the fibrin retention region. Because the fibrin growth is on the exterior of the pellet, blood and agents of fibrin formation are free to communicate with the new fibrin. As with the other device configurations described above, the solid pellet can be coated with a fibrin producing substance such as a growth factor, or may be coated with a thrombophilic substance to help attract and retain blood that is available in the subject tissue. The solid pellet also may be preloaded with an amount of fibrin grown ex-vivo. A pellet placed in a small quantity of blood that has been removed from the patient will become enveloped in fibrin if the combination is placed in an environment conducive to coagulation. A pellet becomes anchored after implantation as the surface of the tissue recoils behind the implant device, surrounding it and filling in the cavity created by the penetration of the implant device and associated delivery device.

Figure 14:
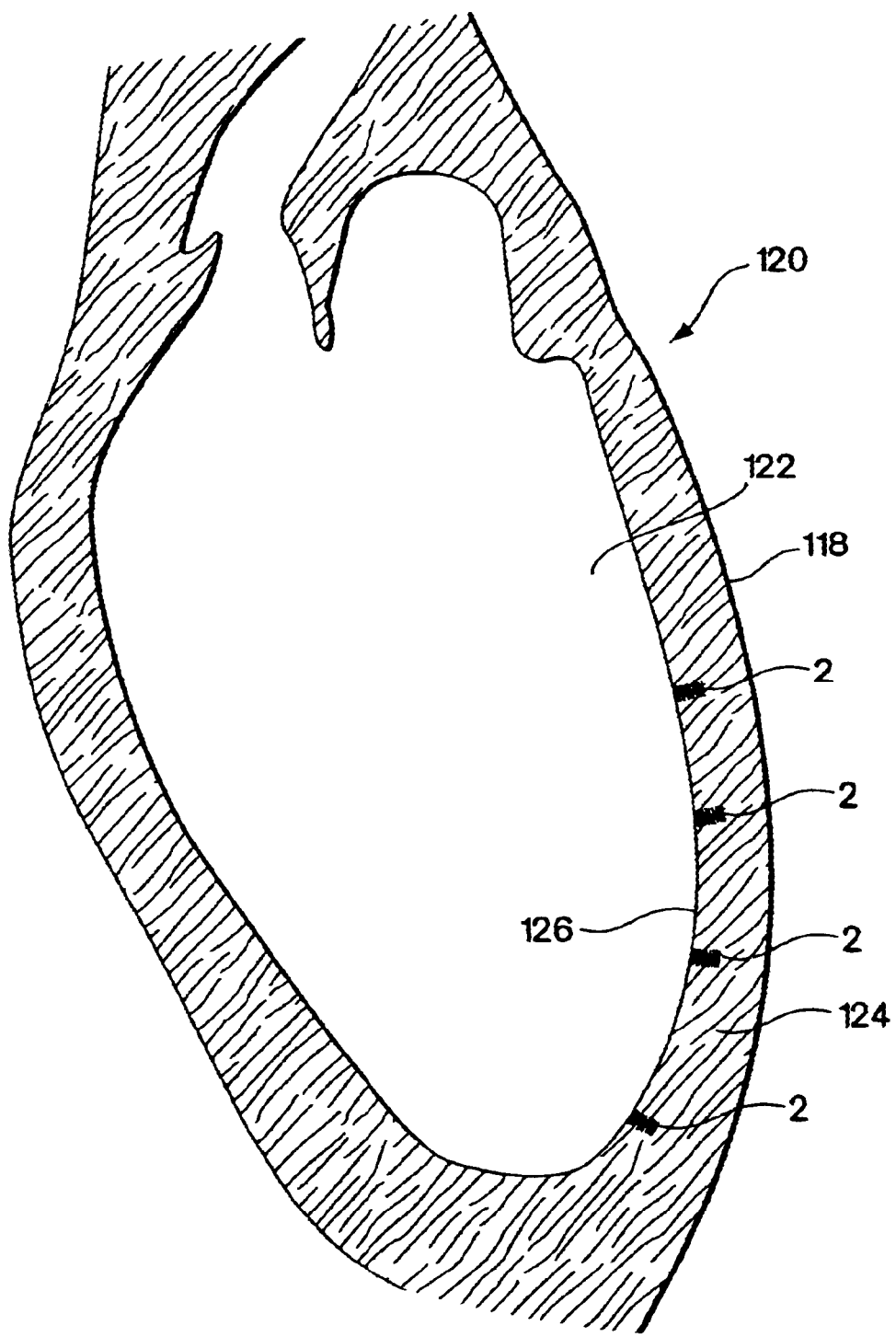
FIG. 14 is a diagramatic cross sectional illustration of the left ventricle of the heart with multiple implant devices placed in the myocardium.
Figure 15A:
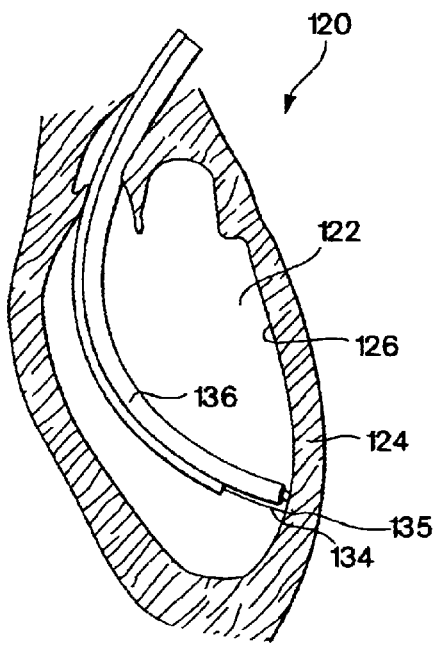
FIGS. 15A–15D are diagramatic illustrations of an implant device being delivered to the myocardium by a percutaneously inserted delivery catheter.
Figure 15B:
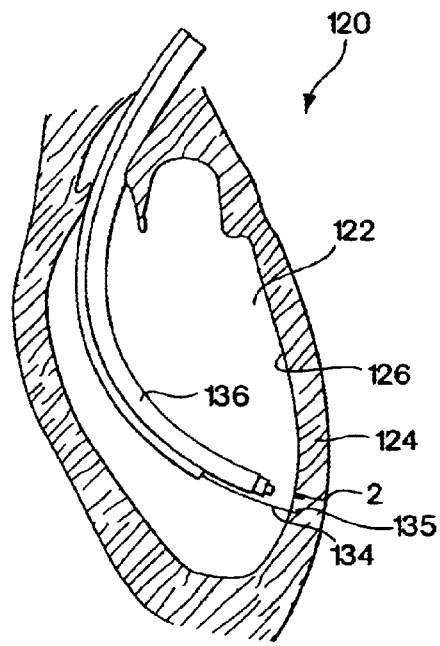
Figure 15C:
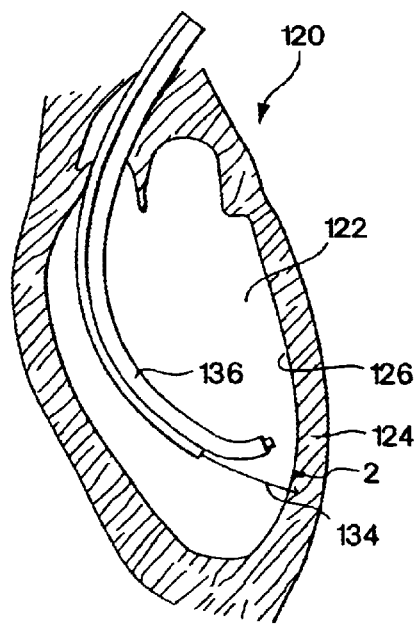
Figure 15D:
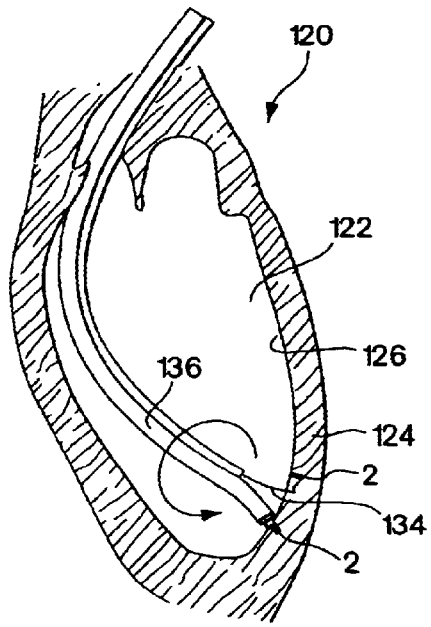

The devices of the present invention may be delivered to their intended tissue location either surgically, by a cut-down method or, percutaneously with a delivery catheter. Multiple devices may be placed within a given area of tissue to be treated. Creating multiple locations of localized fibrin growth within a given area of the ischemic tissue increases the amount of angiogenesis in the ischemic region. Multiple devices also increase the number of vessels that are recruited to the ischemic area. For example, in ischemic myocardial tissue of the heart, multiple implant devices 2 may be placed in the myocardial tissue 124 near the endocardial surface 126, as is shown in FIG. 14. The multiple implant devices 2 may be delivered into the myocardium 124 by use of a delivery catheter percutaneously inserted into the patient and navigated through the vessels into the left vertical 122.

As is shown in FIGS. 15A through 15D, a delivery catheter 136 may be navigated to the left ventricle 122 over a guide wire 134 that has been previously navigated to the ventricle and anchored into the tissue by a barbed distal tip 135. To access the left ventricle of the heart percutaneously, a guide catheter (not shown) may be navigated through the patient's vessels to reach the left ventricle 122 of the heart 120. A barbed tip guidewire 134 may then be inserted through the guide catheter and into the ventricle where it pierces the myocardium 124 and becomes anchored within the tissue. After anchoring the guidewire, the steerable delivery catheter 136 may be advanced over the guidewire to become positioned within the ventricle in close proximity to the endocardium 126 to facilitate delivery of implant devices 2. To facilitate delivery of multiple devices, the guidewire lumen of the delivery catheter 136 may be eccentrically located on the catheter. Therefore, when the catheter is rotated about the guidewire, the center of the catheter will rotate through a circular path as demonstrated in FIGS. 15C and 15D, to encompass a broader delivery area with only a single guidewire placement. The outside diameter of the delivery catheter is preferably less than 100 inch. Additionally, the delivery catheter may be provided with steering capability by means of a pull wire extending the length of the catheter and attached at its distal end such that pulling on the wire from the proximal end causes the distal tip of the catheter to be deflected. The steering capability provides a broader range of delivery area with a single catheterization. A description of the construction of a delivery catheter for reaching multiple sites within the left ventricle is described in U.S. patent application Ser. No. 09/073,118 filed May 5, 1998, the entire disclosure of which is herein incorporated by reference.

Figure 16A:
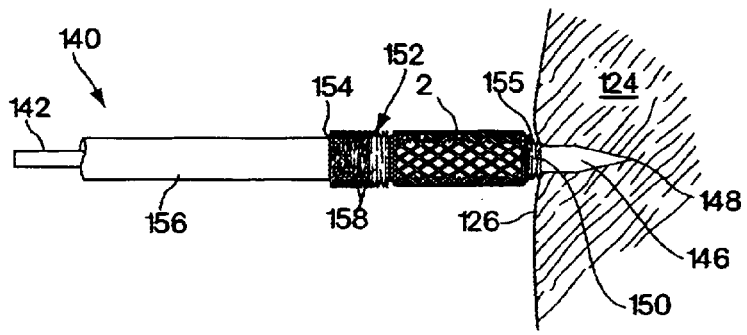
FIG. 16A is a side view of a delivery device carrying an implant device to a tissue location.
Figure 16B:
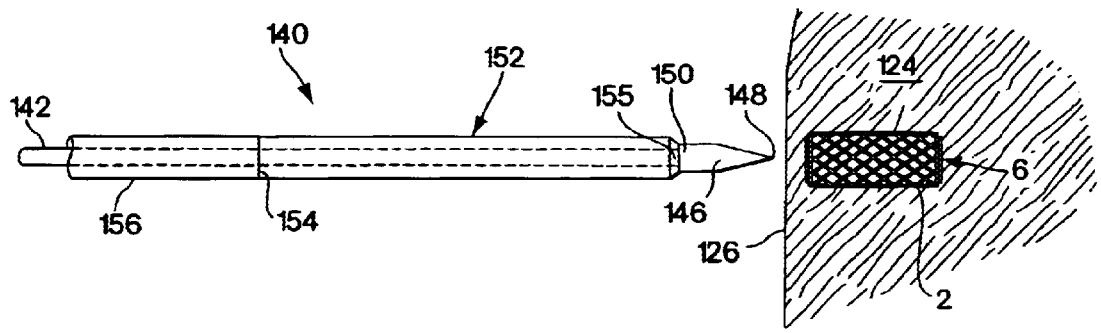
FIG. 16B is a side view of a delivery device after releasing an implant device to a tissue location.

FIGS. 16A and 16B show a side view of a preferred delivery device 140 for the tubular implants 2. The delivery device 140 shown in FIG. 16A may be used with a conventional guide catheter or the steerable catheter 136 discussed above. The delivery device 140 comprises an outer push tube 156 and an independently slidable elongate inner shaft 142 having a sharp obturator head 146 at its distal end. The obturator head 146 is formed at the distal end of the inner shaft 142 by any convenient means and is configured to have a sharp, piercing tip 148. Included in the material that forms the obturator head 146 should be a radiopaque material such as gold or platinum to make the distal area of the device visible under fluoroscopy. Heat bonded to the proximal end 150 of the obturator head 146 is a flexible crinkle tube 152, which may be formed from a material such as polyethylene terephthalate (PET). Attached to the proximal end 154 of the crinkle tube 152 by heat bonding is the push tube 156, which may be formed from a closely wound spring having a PET shrink tube formed around its outer surface to fill in the voids created by the coils. The crinkle tube 152 collapses under compressive load to form a random pattern of folds 158, which serve to increase the overall diameter of the crinkle tube 152 such that it comes into engagement and frictional contact with the interior surface of a hollow or generally tubular implant device 2 placed over it.

When placed in tension as shown in FIG. 16B, the crinkle tube elongates and returns to a low diameter configuration without folds. The configuration of the crinkle tube is manipulated by relative movement of the inner shaft 142, having its obturator 146 joined to the distal end 155 of the crinkle tube, relative to the push tube 156, which is joined to the proximal end of the crinkle tube 154. The inner shaft and push tube are slidable relative to each other and may be made controllable from the proximal end of the device by a suitable handle and core wire extension.

To deliver an implant device 2 to a tissue location, the device first must be loaded over the crinkle tube. The push tube is moved in a distal direction and the core wire is moved in the proximal direction to compress the crinkle tube 152 effectively increasing the diameter of the crinkle tube. The increased diameter crinkle tube engages the interior chamber 6 of an implant device 2, holding it in place for delivery into tissue as shown in FIG. 16A. After being navigated to the intended location within a guide catheter, the distal end of delivery device is then advanced distally out of the guide catheter so that the sharp tip 148 penetrates into the tissue 124 and the device 2 becomes implanted. As shown in FIG. 16B, after delivery into tissue, the crinkle tube may be placed in tension, to withdraw the plurality of folds that engage the interior chamber of the implant 2. After reducing the profile of the crinkle tube 152 the implant device 2 easily slides off the crinkle tube over the obturator 146 and remains in place in the tissue 124. The delivery device is then withdrawn from the tissue.

A pellet delivery catheter 160 suitable for percutaneously delivering the pellet and pellet implants 100 or 110 into tissue is shown in FIGS. 17A and 17B. In the example of delivering an implant device to the myocardium of the heart, the pellet delivery catheter 160 is insertable through a guide catheter such as the steerable delivery catheter 136 discussed above. The pellet delivery catheter 160 shown in FIGS. 17A and 17B slidably receives an inner push tube 164 with a pellet carrier 162 at its distal end. The inner push tube is slidable within the catheter tube 160 and is withdrawn inside the outer tube during delivery to the myocardial site through the steerable catheter discussed above. After reaching the myocardial site, the distal tip of the steerable catheter is moved into contact with the surface of the tissue 126. The inner push tube is moved distally with respect to the catheter 160 to extend the pellet carrier past the distal tip 165 of the catheter and is advanced into the tissue.

The pellet carrier 162 is shaped to have a concave cradle 170 suitable for pushing the pellet 100 through the lumen 161 of the pellet catheter during delivery. Extending distally past the cradle 170 on the pellet carrier is a piercing distal tip 168 that pierces the endocardium 126 at the selected site as the inner push tube 164 is moved distally. As shown in FIG. 17B, continued distal movement of the push tube 164 causes the pellet carrier to penetrate the myocardium through the penetration site initiated by the piercing tip 168. Only the endocardial surface 126 presents any measurable resistance to penetration, and once it is penetrated by the piercing tip 168, continued penetration into the myocardium 124 presents little additional resistance. Therefore, the pellet carrier 162 with a pellet 100 nested within the cradle 170 can penetrate into the myocardium 124 with little resistance or interference with the pellet 100. Once the cradle portion 170 of the pellet carrier 162 has penetrated the endocardial surface, a push wire 172, slidable within the push tube 164 and pellet carrier 162, is moved distally through cradle port 171 to push the pellet 100 from the cradle area 170 so that it becomes implanted within the myocardium 124. After implantation, the push wire 172 and push tube 164 with pellet carrier 162 are withdrawn proximally into the catheter tube 160 so that the steerable delivery catheter 136 may be withdrawn from the ventricle. The piercing tip 168 of the pellet carrier 162 should be sheathed within the catheter tube 160 during entry and withdrawal so as not to inadvertently pierce other areas of tissue.

The catheters and push tube described above may be fabricated from conventional materials known in the art of catheter manufacture. The push wire 172 also may be fabricated from conventional materials known in the guidewire art: stainless steel or a plastic material. The pellet carrier 162 may be fabricated from a rigid polymer or stainless steel and joined to the distal end of the push tube 164 by any conventional means of bonding. The cradle area 170 should be configured to nest and hold the pellet during delivery to permit passage of the push wire 172 through cradle port 171 so that the pellet can be pushed from the cradle into the myocardium. By way of example, the cradle 170 may have a concave, dish-like shape if intended to hold a spherical shaped pellet as has been described.

Figure 18A:
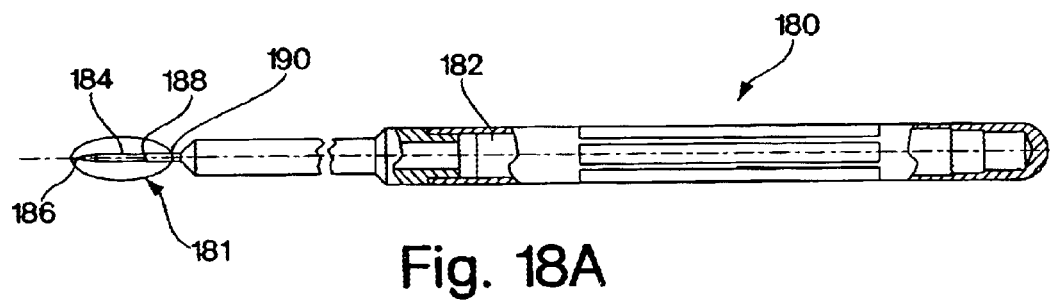
FIG. 18A is a side view of a surgical delivery device.
Figure 18B:
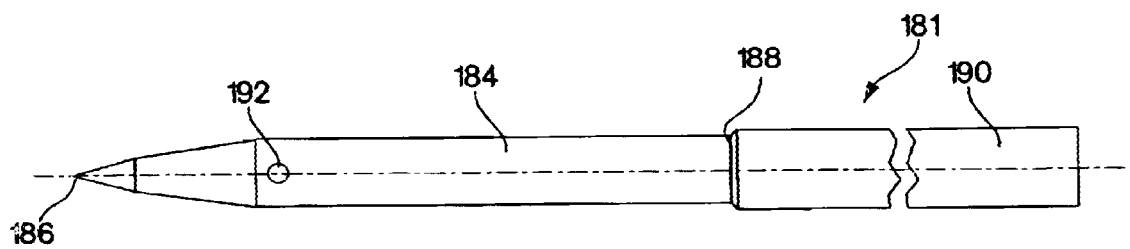
FIG. 18B is a detail of the distal tip of a surgical delivery device.
Figure 18C:
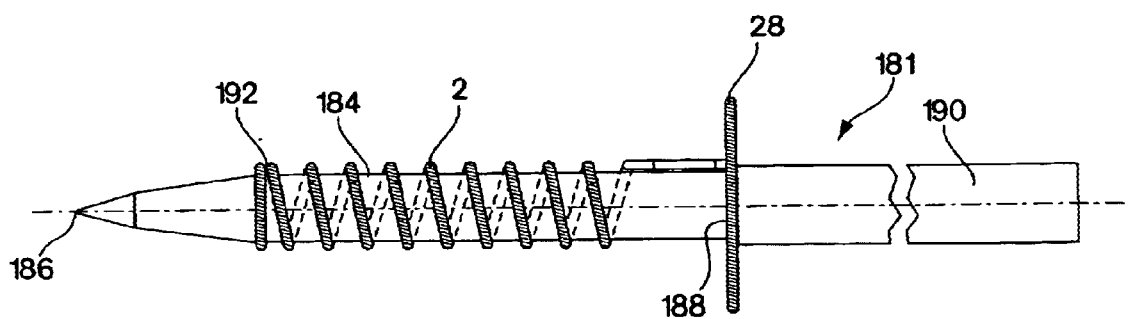
FIG. 18C is a detail of the distal tip of a surgical delivery device carrying an implant device.

The implant devices 2 of the present invention may also be delivered to their intended tissue location surgically. FIGS. 18A–18C show an example of a surgical delivery device that may be used to deliver tubular implants such as those shown in FIGS. 1–7. The delivery device, shown in FIG. 18A, comprises an obturator 180 that includes a main shaft 182, by which it can be gripped and manipulated. The distal end 181 of the shaft 182 is shown in detail in FIG. 18B and includes a reduced diameter device support section 184 having a sharp distal tip 186 adapted to pierce tissue. The diameter of the shaft segment 184 is such as to fit closely within the interior chamber 6 of the devices 2. The proximal end of the segment 184 terminates in a shoulder 188 formed at the junction of a proximally adjacent, slightly enlarged diameter portion 190 of the shaft. The distal end of the device support segment 184 may include a radially projecting pin 192 dimensioned to project and fit between adjacent turns of the coil embodiments 16 and 40. The pin 192 engages the coils 16 and 40 in a thread-like fashion so that after the assembly has been inserted into the tissue, the obturator 180 can be removed simply by unscrewing the obturator to free it from the implanted coil 16 or 40. Alternatively, the obturator may be configured without the projecting pin 192 so that the device can be slipped on and off the obturator, without screwing. When the implant device 2 is mounted on the obturator 180, the proximal end of the device may bear against the shoulder 188, and the tail 28, if so equipped may extend along the segment 190 of the obturator.

In use, the intended tissue location is first accessed surgically, such as by a cut-down method. The obturator, with an implant device loaded on to segment 184, then may be advanced into the tissue to deliver the implant. The sharp tip pierces the tissue permitting the obturator and implant to be pushed inward into the tissue. In the example of delivery to the myocardium, the epicardial surface of the heart is accessed and penetrated by the obturator to deliver the implant. The shoulder 188 prevents proximal movement of the implant along segment 184 during delivery. Preferably, the distal end of the obturator is projected to, and slightly beyond, the endocardium to place the implant device. The obturator then may be unscrewed and separated from the implant device. If the obturator is configured without the pin 192, the obturator may be withdrawn directly from the device and the tissue. Simply applying light closure pressure to the epicardial puncture will cause the puncture hole to clot at the epicardium.

As mentioned above, another aspect of the invention involves introducing a fibrin forming substance directly into the subject tissue, without an associated implant device. Substances that promote fibrin growth include growth factors or thrombin. A thrombophilic substance may also be introduced alone to absorb and retain blood in a given area. The pooled and stagnated will begin to coagulate and form into fibrin. Therefore, though the thrombophilic substance need not be associated with a device it can be considered to provide a fibrin retention region by the nature of its composition. Delivery of fibrin producing substances directly into ischemic tissue may help initiate and intensify fibrin growth as they mix with other agents of fibrin formation present in the blood and tissue available in the region. Delivery of fibrin agents alone provides a simplified method of treating ischemia by promoting revascularization when implantation of a device may be unavailable as an option to the particular patient.

Fibrin producing agents may be delivered directly into tissue by an injection device of any configuration capable of reaching the treatment site. Preferably the agents are delivered in a flowable form so that they may be injected directly into the tissue. To prevent the loss of a flowable agent, it is desirable to maintain the agents suspended in a relatively high viscosity gel form, which is flowable, but less likely to migrate from the intended location than would be a low viscosity liquid. Any device capable of injecting a flowable substance into tissue is suitable for delivery of the agents according to the present method. Therefore, a device such as a conventional needle and syringe could be used to administer the agents.

Figure 19:
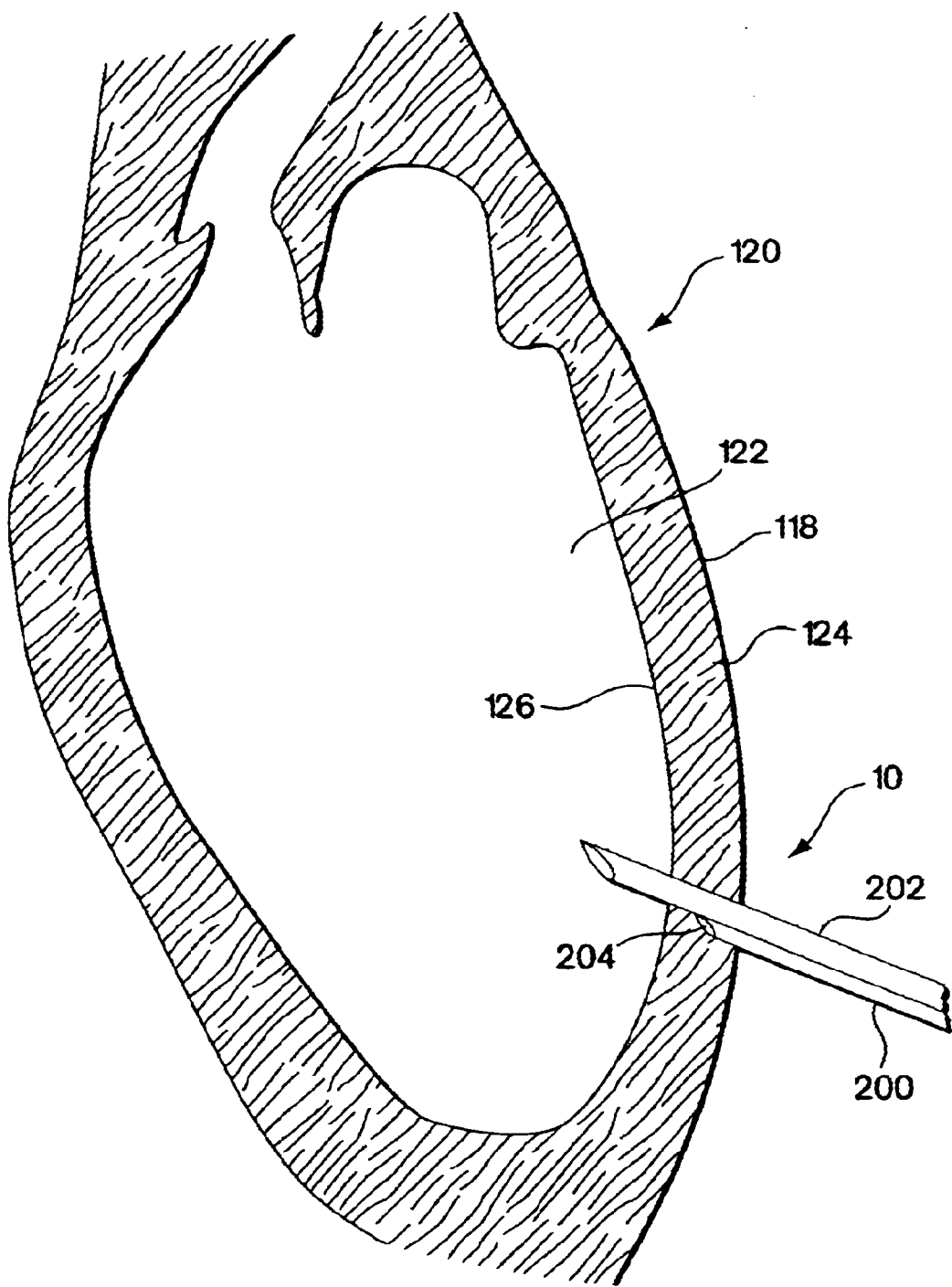
FIG. 19 is a diagramatic illustration of the left ventricle of the heart and a substance delivery device.
Figure 20:
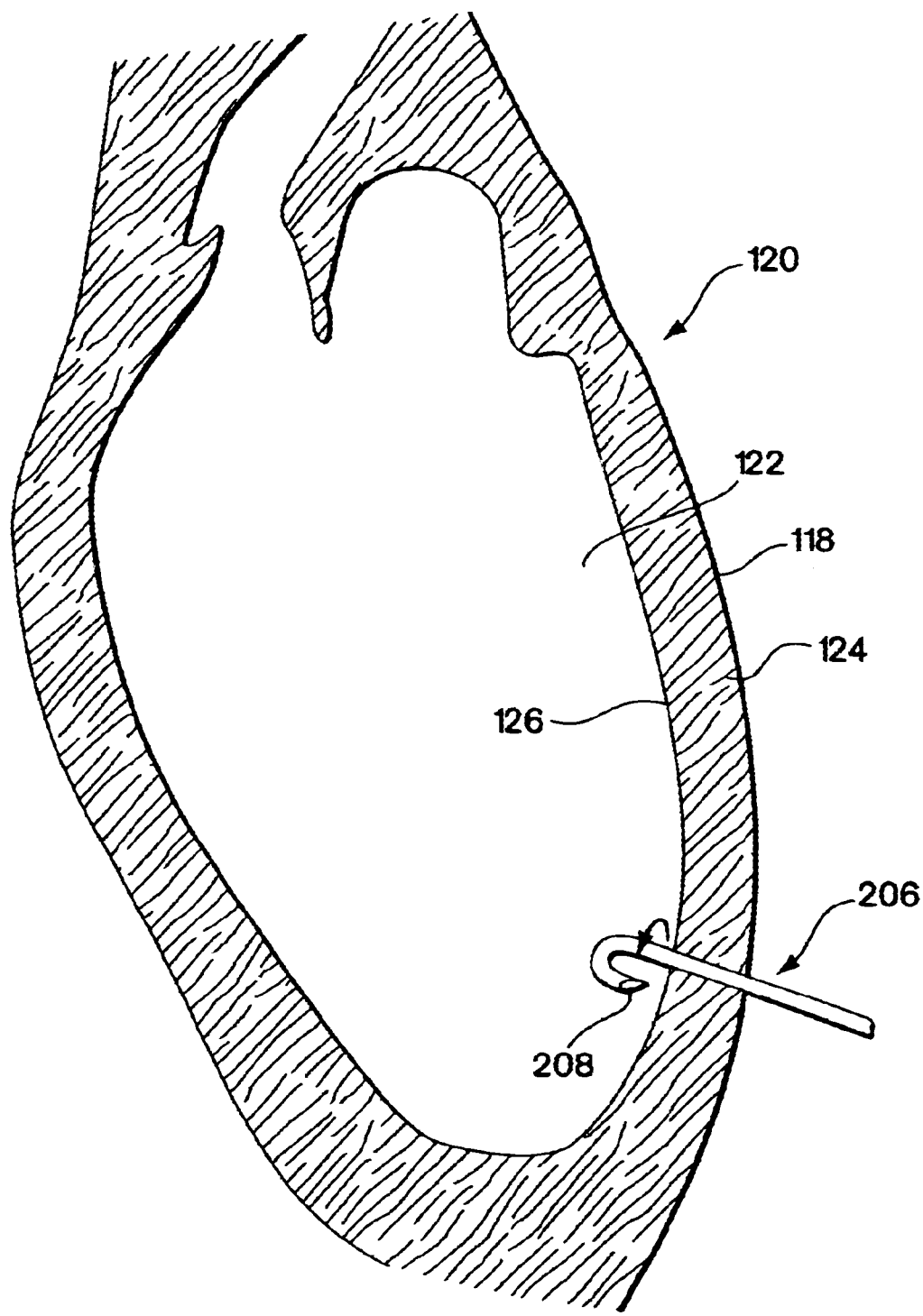
FIG. 20 is a diagramatic illustration of the left ventricle of the heart and a substance delivery device.

Particularly useful devices for transthoracically administering agents to sites in the myocardium is disclosed.in U.S. patent application Ser. No. 09/164,164. The devices disclosed in that application are shown in FIGS. 19 and 20. FIG. 19 shows a delivery tube 200, through which agents are ejected, joined to a pressure sensing tube 202, which monitors pressure such as that produced in the left ventricle 122 of the heart 120. The tubes are staggered relative to each other so that when the pressure tube 202 enters the highly dynamic pressure region of the ventricle, the operator will be alerted that the delivery tube outlet 204 is in the tissue 124 and the agent may be delivered. FIG. 20 shows a steerable delivery tube 206 that may be introduced into the ventricle through the epicardial surface 118, curved, then withdrawn slightly so that the delivery tube opening 208 penetrates the myocardium through the endocardium 126. Removal of the opening 208 from the endocardium permits the delivery tube to be rotated to a new tissue location. In either embodiment transthoracic embodiment 200 or 206, delivery pressure to eject the agent may be created by an external pressure source or a syringe mechanism.

From the foregoing, it will be appreciated that the invention provides a novel approach to the treatment of ischemic tissue by promoting fibrin growth in the tissue. The fibrin growth initiates angiogenesis and vessel recruitment, which revascularizes the area. The devices and methods for promoting fibrin formation are simple and easily applied to the intended tissue with a minimum of steps.

It should be understood, however, that the foregoing description of the invention is intended merely to be illustrative thereof and that other modifications, embodiments and equivalents may be apparent to those skilled in the art without Having thus describe the invention what we desire to claim and Secure by Letters Patent is:

1. A device for promoting fibrin growth in tissue comprising:
    a frame, implantable in tissue, having a fibrin retention region configured to permit communication between fibrin associated with the frame and the surrounding tissue; the frame being securely implantable in the tissue such that the frame and associated fibrin resist migration; and
    a fibrin promoting substance associated with the frame prior to implantation.

2. A device as defined in claim 1 wherein
    the fibrin promoting substance comprises thrombin.

3. A device as defined in claim 1 wherein
    the fibrin promoting substance comprises a growth factor.

4. A device as defined in claim 1 wherein the frame further comprises:
    a hollow interior chamber, which serves as the retention region and the interior chamber is configured to permit communication between the associated fibrin and tissue that surrounds the device when implanted.

5. A device as defined in claim 1 wherein
    the frame is comprised of a biodegradable substance.

6. A device as defined in claim 5 wherein
    the biodegradable substance includes a substance that includes the fibrin promoting substance that is released as the frame degrades.

7. A device as defined in claim 1 wherein the frame further comprises:
    an exterior surface, which comprises a fibrin retention region.

8. A device as defined in claim 1 wherein
    formed fibrin is associated with the fibrin retention region prior to implantation.

9. A device as defined in claim 1 further comprising:
    a thrombophilic substance associated with the device.

10. A method of promoting fibrin growth within tissue comprising:
    providing an implant configured to promote fibrin growth;
    associating formed fibrin with the implant; and
    implanting the implant in tissue.

11. A method of promoting revascularization of biological tissue comprising:
    providing a device having a fibrin retention region configured to be in communication with tissue in which the device is implanted;
    treating the device with a fibrin promoting substance; and
    securely implanting the device within a region of tissue so that it does not migrate from its implant site.

12. A method of promoting revascularization of biological tissue comprising:
    the step of manipulating tissue to initiate fibrin growth within the tissue.

13. A method of promoting revascularization as defined in claim 12 wherein
    multiple tissue sites are manipulated to initiate fibrin growth within an area of tissue.

14. A method of promoting revascularization as defined in claim 12 further comprising:
    placing a fibrin producing substance in the tissue.

15. A method of promoting revascularization as defined in claim 14 wherein
    the fibrin producing substance is injected into the tissue.

16. A method of promoting revascularization as defined in claim 14 wherein
    the fibrin producing substance is associated with a device which is implanted into the tissue.

17. A method of promoting revascularization as defined in claim 16 wherein the device is biodegradable and the associated fibrin producing substance is released with the degradation of the device.

18. A method of promoting revascularization as defined in claim 12 further comprising:

implanting a device having a fibrin retention region to foster fibrin growth.

19. A method of promoting revascularization as defined in claim 18 further comprising:

associating a formed thrombus with the device.

20. A device for treating ischemic biological tissue comprising:

a frame implantable in tissue and configured to foster fibrin growth in the area of the frame while permitting communication between the fibrin growth and surrounding tissue into which the device is implanted;

the frame being securely implantable in the tissue such that the frame and associated fibrin resist migration.

21. A method of treating ischemia comprising:

providing an implant device having a fibrin retention region; associating a formed thrombus with the fibrin retention region of the device; and implanting the device in tissue.

22. A method as defined in claim 21 wherein the device has an interior chamber, which comprises the fibrin retention region and the thrombus is captured within the interior chamber.

23. A method as defined in claim 22 wherein the thrombus is not adhered to the fibrin retention region.

24. A method as defined in claim 21 wherein the thrombus is adhered to the fibrin retention region.

25. A method of revascularizing biological tissue comprising:

providing an implant device configured to promote fibrin growth;

implanting the device in tissue.

26. A method of revascularizing tissue as defined inclaim 25 wherein the tissue is revascularized by angiogenesis and recruitment of existing vessels to the tissue.

27. A device for promoting fibrin growth in tissue comprising a frame, implantable in tissue, having a solid exterior surface that serves as a fibrin retention region and a fibrin promoting substance associated with the exterior surface prior to implantation of the frame.

28. A device for promoting fibrin growth in tissue comprising a frame, implantable in tissue, having a solid exterior surface that serves as a fibrin retention region and formed fibrin associated with the fibrin retention region prior to implantation.

29. A device for promoting fibrin growth in tissue comprising a frame, implantable in tissue, having a solid exterior surface that serves as a fibrin retention region and a thrombophilic substance associated with the fibrin retention region prior to implantation.

* * * * *